(12) United States Patent
Hirase et al.

(10) Patent No.: US 11,898,194 B2
(45) Date of Patent: Feb. 13, 2024

(54) METHOD FOR DETECTING TARGET MOLECULE

(71) Applicant: TOPPAN PRINTING CO., LTD., Taito-ku (JP)

(72) Inventors: Takumi Hirase, Taito-ku (JP); Yoichi Makino, Taito-ku (JP); Yosuke Horiuchi, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 77 days.

(21) Appl. No.: 16/872,855

(22) Filed: May 12, 2020

(65) Prior Publication Data

US 2020/0270674 A1 Aug. 27, 2020

Related U.S. Application Data

(63) Continuation of application No. PCT/JP2018/042362, filed on Nov. 15, 2018.

(30) Foreign Application Priority Data

Nov. 17, 2017 (JP) ................................ 2017-222128

(51) Int. Cl.
*C12Q 1/68* (2018.01)
*C12Q 1/6806* (2018.01)
(Continued)

(52) U.S. Cl.
CPC .......... *C12Q 1/6806* (2013.01); *B01L 3/5027* (2013.01); *C12Q 1/686* (2013.01);
(Continued)

(58) Field of Classification Search
CPC ..... C12Q 1/6806; C12Q 1/686; B01L 3/5027; B01L 2200/0689; B01L 2300/0829; G01N 33/536
See application file for complete search history.

(56) References Cited

U.S. PATENT DOCUMENTS 11,097,269 B2 * 8/2021 Goto ................. B01L 3/502715
2016/0333400 A1 11/2016 Makino et al.
(Continued)

FOREIGN PATENT DOCUMENTS

CN 106596487 A 4/2017
JP 2006-271348 A 10/2006
(Continued)

OTHER PUBLICATIONS

Kroneis et al. (Thesis, "On-chip multiplex PCR identification of automatically retrieved single microchimeric cells", 2009, p. 1-63) (Year: 2009).*

(Continued)

*Primary Examiner* — Stephanie K Mummert
(74) *Attorney, Agent, or Firm* — Oblon, McClelland, Maier & Neustadt, L.L.P.

(57) ABSTRACT

A method for detecting a target molecule, including supplying a liquid dispersion of a structural substance including a target molecule into a well array such that the structural substance is introduced into wells of the well array, supplying a sealing solution into the well array such that a layer of the sealing solution is formed on the liquid dispersion in the wells, and that the liquid dispersion is sealed in the wells, extracting the target molecule from the structural substance, and detecting the target molecule.

20 Claims, 10 Drawing Sheets

Specification includes a Sequence Listing.

(51) Int. Cl.
  *B01L 3/00* (2006.01)
  *C12Q 1/686* (2018.01)
  *G01N 33/536* (2006.01)

(52) U.S. Cl.
  CPC .... *G01N 33/536* (2013.01); *B01L 2200/0689* (2013.01); *B01L 2300/0829* (2013.01)

(56) References Cited

U.S. PATENT DOCUMENTS

| | | |
|---|---|---|
| 2017/0166959 A1 | 6/2017 | Hashimoto et al. |
| 2018/0067038 A1 | 3/2018 | Fathollahi et al. |
| 2018/0196059 A1 | 7/2018 | Makino |
| 2018/0250672 A1 | 9/2018 | Jamshidi et al. |
| 2019/0060897 A1 | 2/2019 | Makino et al. |

FOREIGN PATENT DOCUMENTS

| | | |
|---|---|---|
| JP | 2008-283977 A | 11/2008 |
| JP | 2014-503831 A | 2/2014 |
| JP | 6183471 B2 | 8/2017 |
| KR | 10-1605701 B1 | 4/2016 |
| WO | WO2015/166768 A1 | 11/2015 |
| WO | WO2013/151135 A1 | 12/2015 |
| WO | WO 2016/149639 A1 | 9/2016 |
| WO | WO 2017/043530 A1 | 3/2017 |
| WO | WO 2017/095917 A1 | 6/2017 |
| WO | WO 2017/188441 A1 | 11/2017 |

OTHER PUBLICATIONS

Fang et al. (Anal Chem, 2010, vol. 82, p. 3002-3006) (Year: 2010).*
Battacharyya et al. (Anal Chem, 2006, 788-792) (Year: 2006).*
Kroneis et al. (J Cell Mol Med, 2010, 14(4):954-969) (Year: 2010).*
Kim et al. (Lab Chip, 2012, 12:4986-4991) (Year: 2012).*
Oblath et al. (Lab Chip, 2013, 13, 1325-1332) (Year: 2013).*
Kan et al. (Lab Chip, 2012, vol. 12, 977-985) (Year: 2012).*
Zhang et al. (Anal Chem 2013, 85, 1484-1491) (Year: 2013).*
Extended European Search Report dated Nov. 24, 2020 in European Patent Application No. 18879365.7, 1 pages.
Extended European Search Report dated Nov. 4, 2020 in European Patent Application No. 18879365.7, 43 pages.
Ying Zhu, et al., "Printing 2-Dimentional Droplet Array for Single-Cell Reverse Transcription Quantitative PCR Assay with a Microfluidic Robot" Scientific Reports, vol. 5, No. 1, XP055743284, Apr. 1, 2015, pages 1-7.
Kim et al., "Large-scale femtoliter droplet array for digital counting of single biomolecules," The Royal Society of Chemistry, 6 pages, 2012.
International Search Report dated Feb. 12, 2019 in PCT/JP2018/042362, filed Nov. 15, 2018, (with English Translation).
Chinese Office Action and Search Report dated Feb. 25, 2023, in the Chinese Patent Application No. 201880070652.9 (with English Translation), 16 pages.
Yuka Igarashi et al., "Single Cell-Based Vector Tracing in Patients with ADA-SCID Treated with Stem Cell Gene Therapy" , Molecular Therapy Methods & Clinical Development, vol. 6, Sep. 2017, pp. 8-16.

* cited by examiner

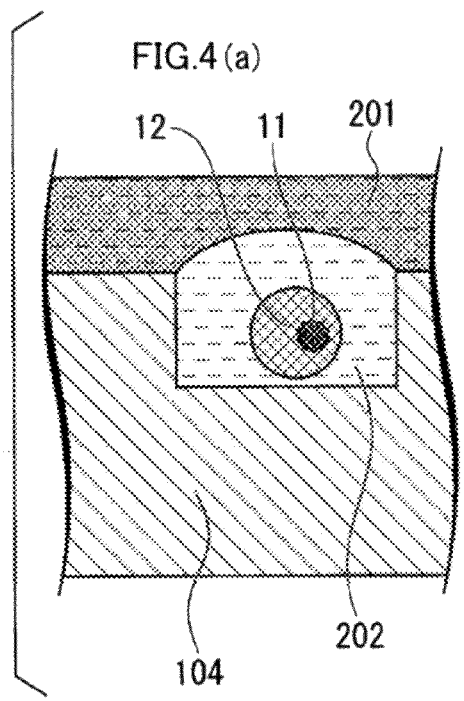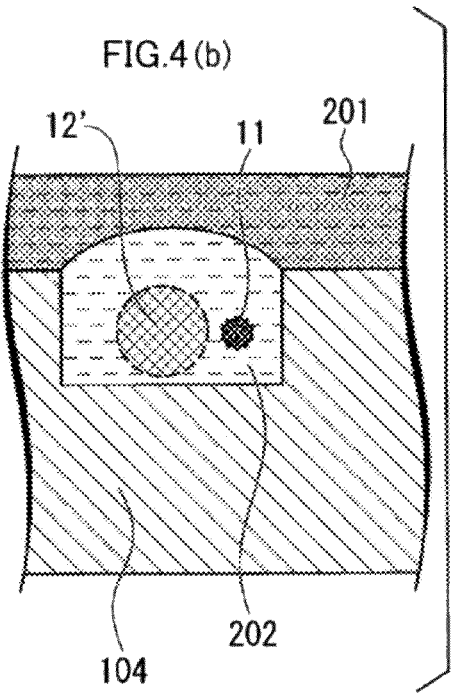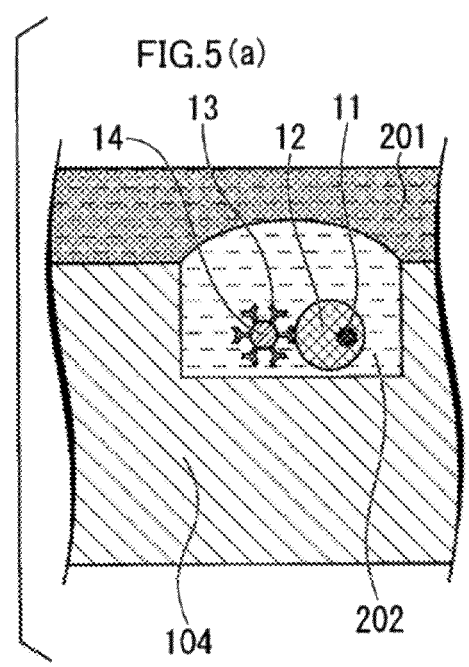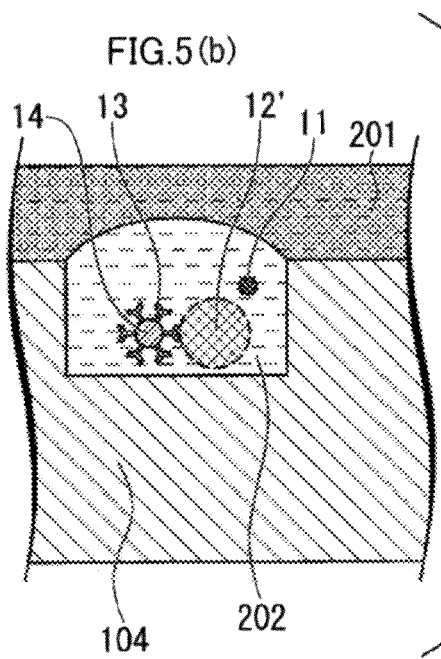

ICA REAGENT
+
Bugbuster

ICA REAGENT ONLY

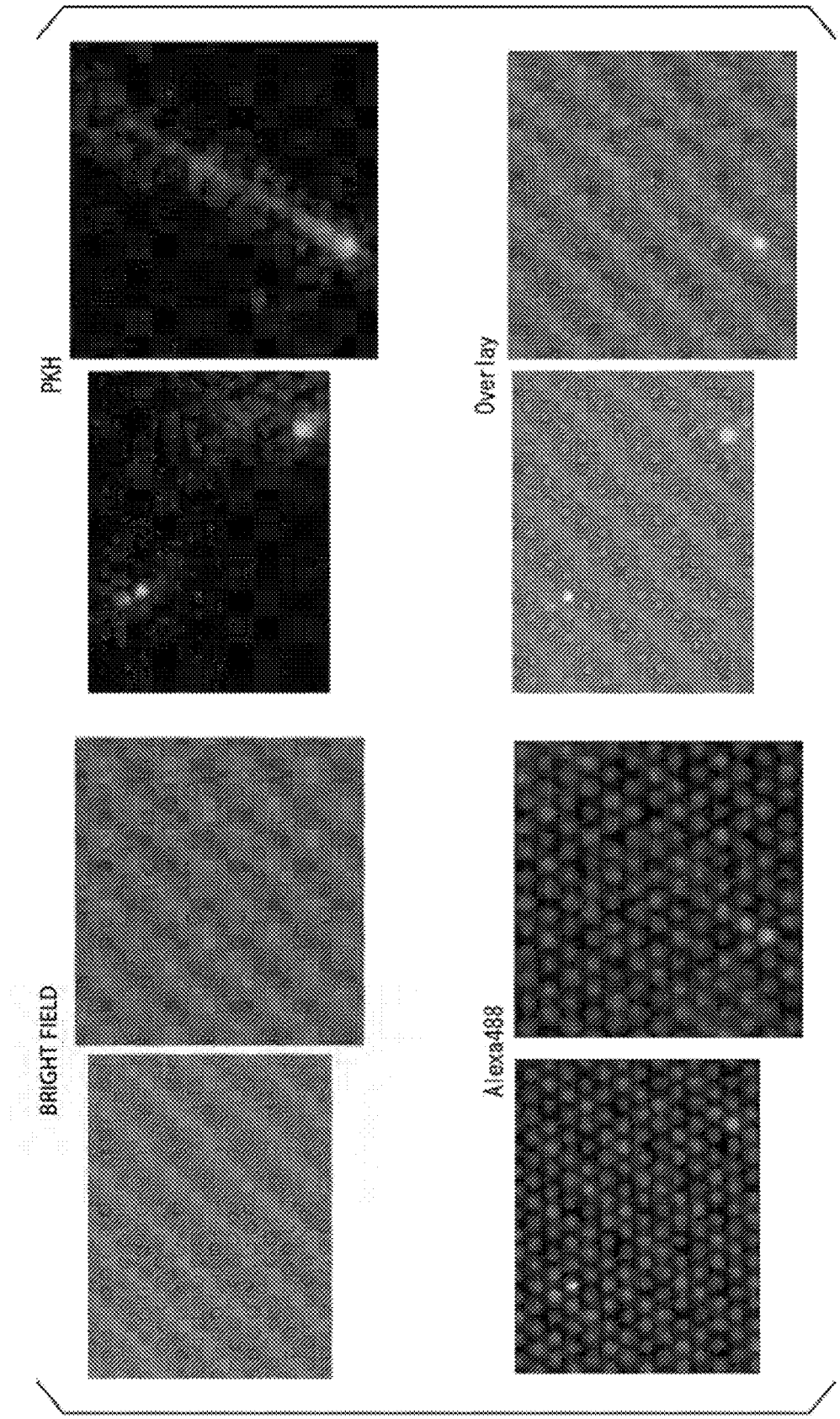

SEQUENCE LISTING

<160> NUMBER OF SEQ ID NOS: 6

<210> SEQ ID NO 1
<211> LENGTH: 140
<212> TYPE: DNA
<213> ORGANISM: Escherichia coli

<400> SEQUENCE: 1
acgttaaaca aaaaatcgtt tcttatttgg attgggataa ataatatggc tgtttatttt    60
gtaactggca aattaggctc tggaaagacg ctcgttagcg ttggtaagat tcaggataaa   120
attgtagctg ggtgcaaaat                                               140

<210> SEQ ID NO 2
<211> LENGTH: 28
<212> TYPE: DNA
<213> ORGANISM: Artificial Sequence
<220> FEATURE:
<223> OTHER INFORMATION: Synthesized DNA named allele probe 1

<400> SEQUENCE: 2
cgcgccgagg gcctaatttg ccagttac                                       28

<210> SEQ ID NO 3
<211> LENGTH: 22
<212> TYPE: DNA
<213> ORGANISM: Artificial Sequence
<220> FEATURE:
<223> OTHER INFORMATION: Synthesized DNA named invader oligo 1

<400> SEQUENCE: 3
gctaacgagc gtctttccag at                                             22

<210> SEQ ID NO 4
<211> LENGTH: 34
<212> TYPE: DNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (1)..(1)
<223> OTHER INFORMATION: Labeled with Alexa488
<220> FEATURE:
<221> NAME/KEY: misc_feature
<222> LOCATION: (4)..(4)
<223> OTHER INFORMATION: Labeled with Black hole quencher-1

<400> SEQUENCE: 4
ttctagccgg ttttccggct gagacctcgg cgcg                                34

<210> SEQ ID NO 5
<211> LENGTH: 24
<212> TYPE: DNA
<213> ORGANISM: Artificial Sequence
<220> FEATURE:

```
<223> OTHER INFORMATION: Synthesized DNA named allele probe 2

<400> SEQUENCE: 5
cgcgccgagg cgcagctcat gccc                                              24

<210> SEQ ID NO 6
<211> LENGTH: 18
<212> TYPE: DNA
<213> ORGANISM: Artificial Sequence
<220> FEATURE:
<223> OTHER INFORMATION: Synthesized DNA named invader oligo 2

<400> SEQUENCE: 6
ccaccgtgca ctcatcaa                                                     18
```

METHOD FOR DETECTING TARGET MOLECULE

CROSS-REFERENCE TO RELATED APPLICATIONS

The present application is a continuation of International Application No. PCT/JP2018/042362, filed Nov. 15, 2018, which is based upon and claims the benefits of priority to Japanese Application No. 2017-222128, filed Nov. 17, 2017. The entire contents of all of the above applications are incorporated herein by reference.

BACKGROUND OF THE INVENTION

Field of the Invention

The present invention relates to a method for detecting a target molecule.

Discussion of the Background

Early detection of disease and prediction of the effects of medication are performed by quantitatively detecting a target molecule in a biological sample. Conventionally, protein quantification has been performed by enzyme-linked immunosorbent assay (ELISA) or the like, and nucleic acid quantification has been performed by the real-time PCR method or the like.

In recent years, there is an increasing need for detecting a target molecule more accurately for the purpose of, for example, finding disease earlier. For example, PTL 1, PTL 2, and NPL 1 disclose techniques for performing an enzyme reaction in a large number of micro compartments as techniques for accurately detecting a target molecule.

These techniques are called digital measurement.

In digital measurement, a sample solution is divided into a large number of minute solutions. Then, a signal from each minute solution is binarized, and the number of target molecules is measured by determining only whether the target molecule is present or not. The digital measurement can significantly improve the detection sensitivity and the quantitativeness compared with conventional methods such as ELISA, real-time PCR method and the like.

In digital PCR, the mixture of a PCR reaction reagent and a nucleic acid is diluted so that the number of template nucleic acids present in a single microdroplet is zero to one. In digital PCR, in order to increase the sensitivity of nucleic acid amplification, and to perform nucleic acid amplification simultaneously for a large number of microdroplets, a smaller volume of each microdroplet is preferred. For example, PTL 3 discloses a microarray reaction vessel in which each well has a volume of 6 nl (nanoliters). In addition, PTL 1 discloses a method in which a sample is introduced into each well by allowing a sample to flow through a flow path over a microarray in which a large number of wells of 3 µm depth and 5 µm diameter are formed in the flow path, after which the excess reagent in the flow path is expelled with a sealant liquid.

PTL 1: JP 6183471 B
PTL 2: JP 2014-503831 A
PTL 3: WO2013/151135
NPL 1: Kim S. H., et al., Large-scale femtoliter droplet array for digital counting of single biomolecules, Lab on a Chip, 12 (23), 4986-4991, 2012.

SUMMARY OF THE INVENTION

According to an aspect of the present invention, a method for detecting a target molecule includes supplying a liquid dispersion of a structural substance including a target molecule into a well array such that the structural substance is introduced into wells of the well array, supplying a sealing solution into the well array such that a layer of the sealing solution is formed on the liquid dispersion in the wells, and that the liquid dispersion is sealed in the wells, extracting the target molecule from the structural substance, and detecting the target molecule.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 4(a) and 4(b) are schematic cross-sectional views illustrating a method for detecting a target molecule in a micro compartment according to a first embodiment.

FIGS. 5(a) and 5(b) are schematic cross-sectional views illustrating a method for detecting a target molecule in a micro compartment according to a second embodiment.

FIG. 15 shows results of fluorescence microscopic observation according to Example 6.

DESCRIPTION OF THE EMBODIMENTS

Figure 1:
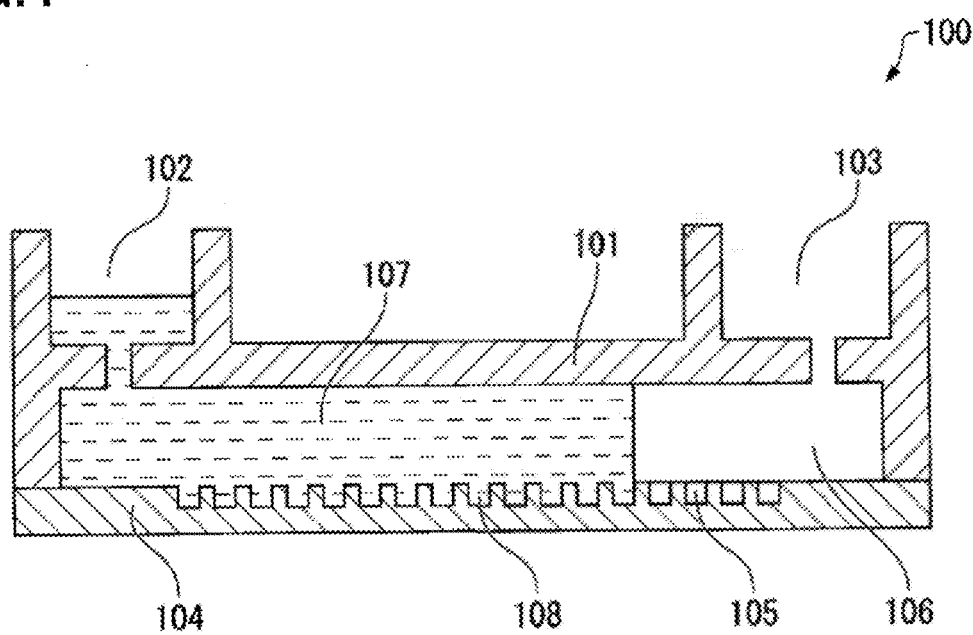
FIG. 1 is a schematic cross-sectional view illustrating a method for supplying a reagent solution to a fluid device.

The embodiments will now be described with reference to the accompanying drawings, wherein like reference numerals designate corresponding or identical elements throughout the various drawings.

With reference to the drawings as appropriate, embodiments of the present invention will be described in detail. Throughout the drawings, the same or corresponding parts are denoted by the same or corresponding reference numerals, and duplicated description is omitted. Further, the drawings are not necessarily to scale, and some of the dimensions are exaggerated for convenience of illustration.

<Fluid Device>

An embodiment of the present invention relates to a method for detecting a target molecule by using a fluid device. A fluid device according to the present embodiment includes a substrate, and a well array disposed on the substrate.

In addition, a fluid device according to the present embodiment may further include a flow path, and a well array disposed in the flow path.

The shape, size, and arrangement of wells are not specifically limited. However, it is preferred to use a well array composed of wells that can accommodate structures for use in a method according to the present embodiment and a predetermined amount of a reagent solution or the like for use in the detection step. The wells may be used without treatment, or may be pre-treated such as by immobilizing an extraction reagent, a detection reagent such as antibody, a specific binding substance, or the like on the inner wall of the wells, or covering the well openings with a lipid bilayer depending on the purpose.

The flow path is a path for supplying a dispersion liquid of a structure or a sealing solution. The shape, structure, volume, or the like of the flow path is not specifically limited. However, it is preferred to use a fluid device having a flow path formed therein configured such that, when a dispersion liquid of a structure is supplied, the structure is introduced into each well of the well array, and, when a sealing solution is inserted, the respective wells are individually sealed to thereby form microdroplets.

In the present embodiment, the flow path in the fluid device may be any internal space as long as a reagent solution, a sealing solution, or the like, which is described later, is introduced and placed therein. The flow path herein may also be referred to as an internal space.

For example, the fluid device may be configured such that a reagent solution (for example, aqueous solution) is dropped to fill the well array, and then a sealing solution (for example, oil) is gently dropped thereon so that the well array is sealed with the sealing solution.

Further, the internal space may also be formed by filling the well array with a reagent solution, sealing the well array with a sealing solution, and covering the well array with a cover member.

(Example of Fluid Device)

FIG. 1 is a schematic cross-sectional view of a fluid device. As shown in FIG. 1, a fluid device 100 includes a substrate 104 and a cover member 101.

The substrate 104 may be made of a light transmitting resin. The substrate 104 according to the present embodiment may be substantially transparent.

The substrate 104 includes a plurality of wells (hereinafter, also referred to as a "well array") 105. The wells 105 of the substrate 104 are open to the surface of the substrate 104. The shape, size, and arrangement of the wells 105 are not limited. However, it is preferred to design the shape, size, and arrangement of the wells 105 so that each structure is suitably introduced into a respective well 105. Typically, the wells 105 are preferably microwells of a small volume. For example, each well 105 may have a volume in a range from 1 aL to 100 fL.

In the example shown in FIG. 1, a plurality of wells 105 having the same shape and the same size are formed in the substrate 104, and each well 105 is capable of accommodating a predetermined amount of reagent solution 107 (dispersion liquid of a structure including a target molecule) for use in a biochemical analysis using the fluid device 100. Further, when particles are used in a biochemical analysis using the fluid device 100, wells 105 having the same shape and the same size may be formed in the substrate 104, and each well 105 may have a shape and size capable of accommodating one or more particles and accommodating a predetermined amount of reagent solution 107 containing particles. The expression "the same shape and the same size" refers to that the shape and the volume are the same to the extent required for digital measurement, and a variation approximately within a manufacturing error may be accepted.

In the fluid device 100, the well 105 may have a diameter of approximately 3 μm and a depth of approximately 4.5 μm, for example. Further, the well 105 may also be arranged in a triangular lattice or a square lattice in the substrate 104.

A region of the substrate 104, which includes a plurality of wells 105, is a region to be filled with the reagent solution 107, which is a target of analysis in the biochemical analysis. In the fluid device 100, a flow path 106 (internal space serving as a flow path) is provided between the substrate 104 and the cover member 101 inside the region to be filled with the reagent solution 107 (internal space).

Further, in the present embodiment, the flow path 106 in the fluid device 100 may be any internal space as long as liquid such as the reagent solution 107 or a sealing solution 201, which is described later, is introduced and placed therein. The flow path 106 herein may also be referred to as an internal space.

For example, the fluid device 100 may be configured such that a reagent solution 107 (for example, aqueous solution) is dropped to fill a plurality of wells 105 (well array), and then the sealing solution 201 (for example, oil) is gently dropped thereon so that the plurality of wells 105 are sealed with the sealing solution 201.

The cover member 101 may be welded or bonded to the substrate 104. For example, the cover member 101 is preferably made of a resin having low autofluorescence, and may also be made of a thermoplastic resin such as a cycloolefin polymer or a cycloolefin copolymer. Further, the cover member 101 may also be formed of a material that does not transmit light of a wavelength near the wavelength detected in fluorescence observation of a signal, or a material that only partially transmits light. For example, a thermoplastic resin to which carbon or metal particles are added may also be used.

The substrate 104 is formed of, for example, a resin. Although the type of the resin is not specifically limited, it is preferred to use a resin that is resistant to a reagent and a sealing solution used in forming droplets. Further, in fluorescence observation of a signal, it is preferred to select a resin with low autofluorescence. For example, a cycloolefin polymer, a cycloolefin copolymer, silicone, polypropylene, polycarbonate, polystyrene, polyethylene, polyvinyl acetate, a fluororesin, or an amorphous fluororesin may be used. These example materials of the substrate 104 are merely illustrative, and do not limit the material of the substrate 104.

The substrate 104 may have a plurality of wells 105 formed on one surface in the thickness direction. A forming method using a resin may be thermal imprinting or optical imprinting as well as injection molding. In addition, when a fluororesin is used, for example, a layer of CYTOP (registered trademark) (AGC Inc.) is formed on the substrate 104, and fine apertures formed in the CYTOP (registered trademark) may serve as the wells 105.

The cover member 101 is formed to have a protruding portion on a surface that faces the substrate 104 when assembled.

For example, a fluid of a thermoplastic resin may be molded into a plate shape having a protruding portion by using a mold. In addition, the cover member 101 may be formed to have a liquid supply port 102 and a liquid discharge port 103.

Once the cover member 101 and the substrate 104 are formed as described above, the cover member 101 and the substrate 104 are stacked with the protruding portion of the cover member being in contact with the surface of the substrate 104 to which the wells 105 are open. Thus, the flow path 106 is formed. Further, the cover member 101 and the substrate 104 are welded to each other by laser welding or the like while being stacked as described above.

<Conventional Detection Method>

Figure 2:
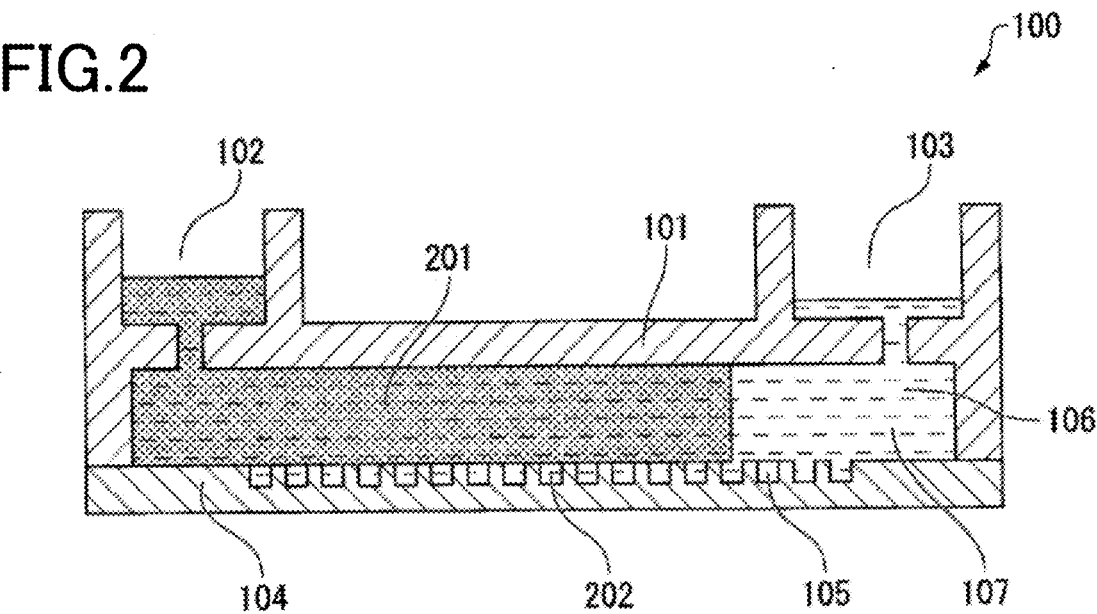
FIG. 2 is a schematic cross-sectional view illustrating a method for supplying oil to a fluid device.
Figure 3:
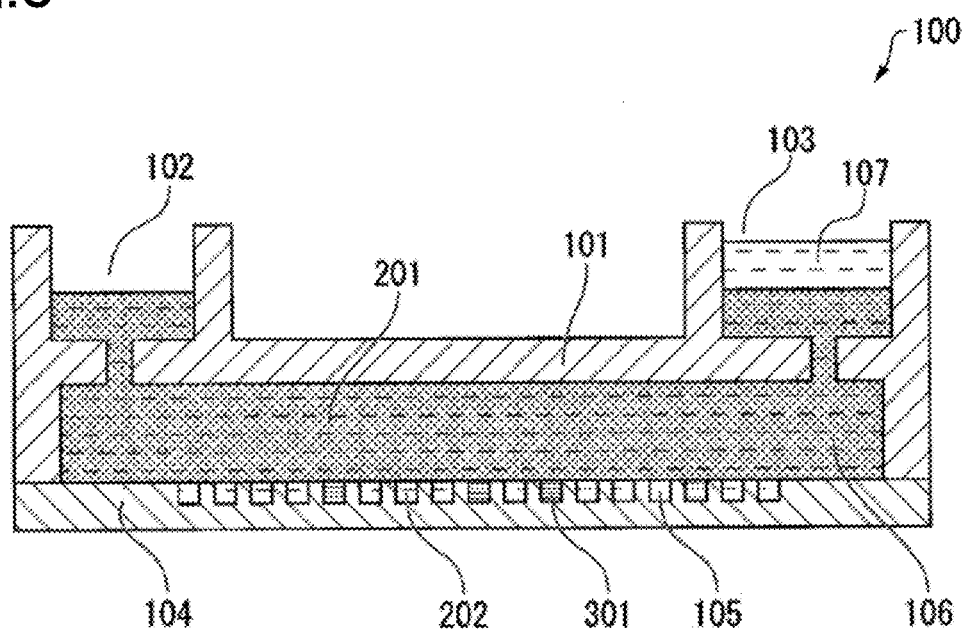
FIG. 3 is a schematic cross-sectional view illustrating a method for detecting a signal from a fluid device.

Referring to FIGS. 1 to 3 showing schematic cross-sectional views of a typical fluid device, a conventional method for detecting a target molecule by using a fluid device will be described.

First, as shown in FIG. 1, the reagent solution 107, which is diluted so that each target molecule is accommodated in a respective well of the wells 105 of the fluid device 100, is supplied from the liquid supply port 102 of the cover member 101 into the flow path 106 between the substrate 104 and the cover member 101. In the liquid supplying step, the reagent solution 107 supplied into the flow path 106 between the substrate 104 and the cover member 101 is accommodated in the plurality of wells 105. Then, as shown in FIG. 2, the sealing solution 201 such as oil is supplied from the liquid supply port 102 of the cover member 101 into the flow path 106 between the substrate 104 and the cover member 101 to individually seal the plurality of wells 105. In the sealing step, the sealing solution 201 substitutes for the reagent solution 107 that has been supplied into the flow path 106 between the substrate 104 and the cover member 101 in the above liquid supplying step and is not accommodated in the plurality of wells 105. As a result, the sealant liquid 201 individually seals the plurality of wells 105 to provide the wells 105 as independent reaction spaces (micro compartments 202). Then, as shown in FIG. 3, a predetermined biochemical reaction (reaction step) is performed in the wells 105. Subsequently, a signal amplified by a signal amplification reaction in the reaction step is observed.

In the conventional detection method, in detection of a target molecule such as a nucleic acid or a protein contained in a structure such as a cell or a virus, a target molecule is extracted from the structure in advance, and supplied as the reagent solution 107 in the liquid supplying step. In this case, some of the target molecules may be lost and their number reduced during extraction of the target molecule from the structure and in the liquid supplying step. In addition, there may be a case where target molecules are not distributed into the wells 105 and left in the flow path 106. Such target molecules are expelled by the sealing solution 201 in the sealing step, resulting in a failure in observation of a signal amplification reaction in the reaction step, and thus a failure in detection of the presence.

As described above, in the conventional detection method, the target molecules contained in the structure may not be correctly detected when the target molecules are not successfully distributed into the respective wells in the liquid supplying step and the sealing step.

<Method for Detecting Target Molecule>

A method for detecting a target molecule according to a first embodiment of the present invention includes the steps of: providing a fluid device having a substrate and a well array disposed on the substrate, supplying a dispersion liquid of a structure including a target molecule into the well array of the fluid device, and introducing the structure into wells of the well array; supplying a sealing solution into the well array, forming a layer of the sealing solution on the dispersion liquid introduced in the wells, and sealing the dispersion liquid in the wells; extracting the target molecule from the structure; and detecting the target molecule.

Further, in the present embodiment, when the fluid device includes a flow path, a method for detecting a target molecule according to the present embodiment may include the steps of: providing a fluid device having a flow path and a well array disposed in the flow path, supplying a dispersion liquid of a structure including a target molecule into the flow path of the fluid device, and introducing the structure into wells of the well array; supplying a sealing solution into the flow path, forming a layer of the sealing solution on the dispersion liquid introduced in the wells, and sealing the dispersion liquid in the wells; extracting the target molecule from the structure; and detecting the target molecule.

According to the detection method of the present embodiment, since the number of target molecules that are lost without being distributed into the wells is reduced, the detection accuracy is improved. Further, since a step of extracting a target molecule from the structure in advance is not required, a target molecule can be detected in a convenient manner. Each of the steps will now be described in detail.

(Step of Introducing Structures into Wells)

In this step, a dispersion liquid of a structure including a target molecule is supplied into a fluid device (a flow path in the fluid device) so that the structures are introduced into the wells of the well array.

The structure is not specifically limited, and any structure may be used. Specific examples of the structure include an exosome, cell, bacterium, virus, fungus, and endoplasmic reticulum in a biological sample. The biological sample may be serum, plasma, urine, or the like, but is not limited thereto.

The structure includes a target molecule. In the present specification, the expression that the structure "includes" a target molecule can refer to that the structure includes a target molecule or that a part or the entirety of target molecule is present on the surface of the structure. Specific examples of the target molecule include nucleic acids such as DNA, RNA, miRNA, and mRNA, structural proteins, proteins such as enzymes, sugars, and lipids.

Liquid for dispersing structures may be one generally used in a biochemical analysis performed by using a fluid device, and is preferably an aqueous solution. Surfactant or the like may also be included in order to facilitate sealing of the well with liquid. In addition, a reagent or the like which is necessary in the step of extracting the target molecule or a step of detecting the target molecule, described later, may also be included. For example, when an invasive cleavage assay (ICA) reaction is used for detection of the target molecule, an ICA reaction agent such as allele probe, ICA oligo, flap endonuclease-1 (FEN-1), or a fluorogenic substrate may also be included in the liquid for dispersing structures.

The expression that the structures are "introduced" into the wells refers to that the structures are distributed into the respective wells of the well array. For example, structures may be introduced into the wells so that the entirety of the structure in which the target molecule is included in a microdroplet is encapsulated (accommodated), or structures may be positioned in the upper part of the respective wells so that only target molecules are introduced into the wells when an extraction step, described later, is performed while the structures are positioned in the upper part of the respective wells. Specific examples of the latter include a technique in which a virus as a structure is adhered to a lipid bilayer that covers the opening in the upper part of the well, and an RNA is extracted by using a virus infection mechanism so that only the extracted RNA is introduced into the well. That is, in this example, the introduction step and the extraction step are performed at the same time.

The number of structures introduced in each well in the introduction step is not specifically limited. Preferably, 0 or 1 structure is introduced into each well. Accordingly, the structure can be detected in units of one piece, that is, digital measurement can be performed. Further, the structure is not necessarily introduced into every well of the well array.

A means for introducing the structure into the well is not specifically limited, and an appropriate means for the selected structure can be used. For example, structures may precipitate by their own weight in the fluid device (in the flow path), and distributed into the respective wells. Alternatively, a substance (capture substance) that captures a structure may be used. The structures that are unlikely to precipitate by their own weight can be bound to the capture substances when they are supplied, or the capture substances can be immobilized in the wells in advance so as to capture the supplied structures. Accordingly, the introduction efficiency can be improved.

(Step of Sealing)

In this step, a sealing solution is supplied into the internal space (for example, flow path) of the fluid device to form a sealing solution layer on the liquid introduced into the wells to thereby seal the liquid in the wells. Thus, microdroplets are formed in the wells in this step.

Further, in this step, a reagent solution (for example, aqueous solution) may be first dropped to fill the well array in the fluid device, and then a sealing solution (for example, oil) may be gently dropped thereon so that the well array is sealed with the sealing solution.

The sealing solution is a liquid that can individually seal the liquid introduced in the plurality of wells to prevent mixture of the liquid and form liquid droplets (microdroplets). The sealing solution is preferably an oily solution, and more preferably an oil. Examples of the oil include fluorine-based oil, silicone-based oil, hydrocarbon-based oil, and a mixture thereof. More specifically, oil manufactured by Sigma under a product name "FC-40" or the like can be used.

(Step of Extracting Target Molecule from Structure)

In this step, the target molecule is extracted from the structure. In the extraction step, all the target molecules may be extracted from the structure, or only part of the target molecules may be extracted from the structure.

The method for extracting a target molecule from the structure is not specifically limited, and known techniques can be used. For example, physical techniques such as heat, ultrasonic waves, light, magnetic force, and electromagnetic waves, chemical techniques such as surfactants, antibiotics, osmotic pressure inducers, and necrosis or apoptosis inducers, and biological techniques such as enzymes, viruses, and phages may be used.

More specifically, when heat is used for the extraction, the fluid device is heated at 70° C. or more, preferably 75° C. or more, e.g., approximately 80° C., for at least 5 minutes, preferably at least 10 minutes, e.g., approximately 15 minutes or approximately 30 minutes to thereby extract the target molecule from the structure.

In a specific example of extraction by using a biological technique, a phage such as an fl phage may be infected with a bacterium such as E. coli to cause bacteriolysis. In another specific example of the extraction by using a biological technique, a nucleic acid may be eluted as the target molecule from a phage such as an fl phage as the structure. More specifically, when a phage (structure) is brought into contact with a bacterium, the phage first recognizes a surface membrane structure (protein, lipid bilayer) of the bacterium and binds thereto. Then, a nucleic acid (target molecule) is injected from the phage into the bacterium. Then, the nucleic acid is replicated in the bacterium to generate a new phage. Thereafter, a cell membrane of the bacterial cell is disrupted (bacteriolysis) by the action of the phage generated in the bacterial cell so that the DNA of the target molecule that has been injected and replicated is released. Alternatively, instead of the bacteriolysis from the inside by the action of the phage, the bacterial cell may be disrupted by an external force such as heat to extract the phage therein. Further, in the case described above, without using a bacterium itself, a lipid bilayer-like substance that mimics a membrane structure of a bacterium may also be used. By adhering a phage to the lipid bilayer-like substance, a nucleic acid contained in a phage can be eluted out from the phage as in the case of adhering to a bacterial cell. In such a case, the step of bacteriolysis may not be performed.

The step of extracting the target molecule from the structure may also be performed in the well after the well is sealed. This can prevent loss of the target molecule. As a result, the target molecule can be detected with high accuracy compared with a conventional method in which the target molecule is distributed into the respective wells of a micro array by using a flow path after they are extracted from the structure.

(Step of Detecting Target Molecule)

In this step, the target molecule is detected. Any known detection method can be used as the method for detecting the target molecule depending on the characteristics of the target molecule to be detected. For example, a reaction for amplifying a signal derived from the target molecule to a detectable level (signal amplification reaction) can be first performed as necessary, and then the amplified signal can be detected by using an appropriate means. In the present embodiment, the step of detecting the target molecule is performed by detecting a nucleic acid.

Examples of the signal that can be used in the detection method according to the present embodiment include fluorescence, chemiluminescence, color development, potential change, and pH change.

The signal amplification reaction may be, for example, a biochemical reaction, and more specifically, an enzymatic reaction. As an example, the signal amplification reaction is an isothermal reaction in which, while a reagent solution containing an enzyme for signal amplification is accommodated in the wells, the fluid device is maintained at a constant temperature condition under which a desired enzyme activity is obtained, for example, 60° C. or more, and preferably approximately 66° C., for a predetermined period of time, for example, at least 10 minutes, and preferably approximately 15 minutes.

Specific examples of the signal amplification reaction include, when a reaction detecting a nucleic acid is used, an ICA reaction such as an Invader (registered trademark) method, LAMP method (registered trademark), TaqMan (registered trademark) method, and fluorescent probe method. In particular, use of an ICA reaction is preferred. This is related to the principle of the ICA reaction that the signal amplification proceeds by two reaction cycles of (1) complementary binding between nucleic acids, and (2) recognition and cleavage of a triple-stranded structure by an enzyme. In such a signal amplification reaction, influence of contaminants other than the target molecule on the reaction cycle is small. Therefore, even if various components present in the structure other than the target molecule are released into a micro compartment in the extraction step, the target molecule can be accurately detected by using the ICA reaction. For example, when an ICA reaction is used for the signal amplification reaction, a liquid for introducing the structure into the well (liquid for dispersing the structure) includes a reaction reagent and a template nucleic acid required for the ICA reaction. When the biochemical reaction in the reaction step is an ICA reaction, and the target molecule is present in the well due to an enzymatic reaction due to the isothermal reaction, a fluorescent substance is released from the quenching substance, which results in a specified fluorescence signal being emitted corresponding to the excitation light.

Alternatively, the target molecule can also be detected by binding a substance specifically binding to the target molecule (specific binding substance) to the target molecule, and detecting the specific binding substance that has been bound. For example, when the target molecule is a protein, ELISA can be used for detection. More specifically, the detection may also be performed by, for example, sandwich ELISA using the principle of FRET. In performing sandwich ELISA using the principle of FRET, first, a first specific binding substance (e.g., antibody) labeled with a first fluorescent substance (donor), and a second specific binding substance labeled with a second fluorescent substance (acceptor) and having a light-absorbing wavelength that overlaps a fluorescence wavelength of the first fluorescent substance are prepared. Then, a target molecule (e.g., antigen) is brought into contact with both the first specific binding substance and the second specific binding substance to form a composite. Once a composite is formed, a distance between the donor and the acceptor decreases, and the fluorescence wavelength of the acceptor can be detected by irradiation of the excitation wavelength of the donor. Alternatively, the specific binding substance may be labeled with a nucleic acid fragment, and then the nucleic acid fragment can be detected by the ICA reaction.

Examples of the specific binding substance include those similar to the specific binding molecules for the structures, which will be described later, such as antibodies, antibody fragments, and aptamers. In order to detect a specific binding substance bound to the target molecule, the specific binding substance may be directly or indirectly labeled by, for example, an enzyme such as horseradish peroxidase (HRP). When two or more specific binding substances are used, each of the specific binding molecules are labeled so that each can be identified.

A signal observation method may be selected from known appropriate methods depending on the type of the signal to be observed. For example, when bright field observation is performed, white light is irradiated in a vertical direction to the substrate provided with the well array. When fluorescence signal observation is performed, excitation light corresponding to the fluorescent substance is irradiated into the well via the bottom of the well to observe fluorescence emitted from the fluorescent substance. An image of the entirety or a part of the observed well array is acquired and stored, and then image processing is performed by a computer system.

(Example of Detection Step)

In the present embodiment, one target molecule can be detected by using two or more specific binding substances. For example, one type of protein can be detected by using two types of monoclonal antibodies that recognize different epitopes. Accordingly, even if the specific binding substance causes misrecognition, or similar target molecules are present in the well, an intended target molecule can be detected with high accuracy.

The method for detecting a target molecule according to the present embodiment can detect two or more types of target molecules. In this case, these target molecules can be detected in any order. For example, when two types of target molecules are detected, the two types of target molecules may be simultaneously detected in a single detection step, or may be separately detected in two independent detection steps. Accordingly, a plurality of target molecules included in the structure can be detected.

Further, since the detection method according to the present embodiment performs the extraction step after the structures are distributed into respective microdroplets, the structures can be individually associated with the detection data of each target molecule and evaluated.

When two or more types of target molecules are simultaneously detected, or when coexisting target molecules, which are detectable even if not simultaneously, are sequentially detected, it is necessary to design a reaction system so that signals indicating the presence of each target molecule are not confused. For example, when detection is performed by using a fluorescence signal, the first target molecule and the second target molecule can be different in wavelength of excitation light and fluorescence so that they can be independently detected by fluorescence without interfering with each other.

The method for detecting a target molecule according to the present embodiment may further include a step of detecting the target molecule prior to the extraction step. In this step, the target molecule included in the structure is detected without being extracted from the structure. The target molecule detected in this step may be a target molecule present on the surface of the structure or may be a target molecule present inside the structure.

When the detection step is performed before the extraction step, the detection step can be performed preferably at a temperature lower than the temperature at which a target component is extracted, and more specifically, at a temperature in the range from room temperature to approximately 60° C.

The steps described in detail above can be performed in sequence as described above. By performing the steps in this order (for example, performing the step of detecting the target molecule after the step of extracting the target molecule), the target molecule extracted from the structure can be detected while being left in the well. Accordingly, an intended target molecule can be detected with high accuracy. Alternatively, the steps may be performed in a different order, or two steps may be simultaneously performed. For example, the extraction step may be performed after the introduction step and before the sealing step. In such a case, the introduction step and the extraction step may be simultaneously performed. Further, when a plurality of detection steps are performed as described above, some of the plurality of detection steps may be performed before the extraction step.

<Detection Method Further Including Step of Detecting Structure>

The detection method according to an embodiment of the present invention may further include a step of detecting the structure in the method for detecting the target molecule according to the embodiment. The step of detecting the structure can be performed at any time during the method for detecting the target molecule, and, for example, may be performed after the step of introducing the structure into the well and before the step of extracting the target molecule from the structure. Alternatively, the structure can be detected after the target substance is extracted from the structure.

In the method according to a specific embodiment of the invention, the step of detecting the target molecule and the detecting the structure can be simultaneously performed.

Further, in the case of performing the simultaneous detection, the reaction system is devised to prevent mutual interference as in the case of simultaneously detecting two or more types of target molecules described above.

In addition, in the case of extracting the target molecule inside the well, it is possible to confirm that the target molecule is definitely extracted from the structure by extracting the target molecule inside the well.

For example, the detection of the structure may be directly performed by observing the structure in a bright field, or may be indirectly performed by detecting the target molecule contained in the structure by performing the same operation as in the above detection step. Examples of the latter include a method using a fluorescent dye for staining a cell membrane, and a method using an antibody or the like that recognizes a virus coat protein.

Regarding the method for detecting the target molecule according to the above embodiment of the present invention, more specific embodiments will be described below.

First Embodiment

A method for detecting a target molecule according to the first embodiment will be described. The present embodiment includes the steps of introducing a structure having a target molecule into a well, sealing the well, extracting the target molecule from the structure, and detecting the target molecule. FIGS. 4(a) and 4(b) are schematic cross-sectional views illustrating a method for detecting the target molecule in a micro compartment according to the present embodiment.

First, structures including a target molecule are introduced into wells. The step of introducing the structures into the wells is performed by, for example, as shown in FIG. 1, supplying the reagent solution 107 into the flow path 106 to thereby distribute the structures into the wells 105.

Next, as shown in FIG. 2, the sealing solution 201 is supplied into the flow path 106 to individually seal the wells 105 to form the micro compartments 202.

In FIG. 4(a), the structure 12 including the target molecule 11 is accommodated in the micro compartment 202 formed of the substrate 104 and the sealing solution 201. Subsequently, in the sealed well, the target molecule is extracted from the structure.

In FIG. 4(b), the target molecule 11 has been extracted from the structure 12' after extraction.

Subsequently, in the reaction step, the target molecule is detected by performing a signal amplification reaction on the target molecule extracted in the well as in the conventional detection method.

Second Embodiment

A method for detecting a target molecule according to the second embodiment will be described. The present embodiment further includes a step of binding a capture substance to the structure in the method according to the first embodiment. FIGS. 5(a) and 5(b) are schematic cross-sectional views illustrating a method for detecting the target molecule in a micro compartment according to the present embodiment.

In FIG. 5(a), the structure 12 including the target molecule 11, the specific binding substance 13, and the capture substance 14 is accommodated in the micro compartment 202 formed of the substrate 104 and the sealing solution 201.

The specific binding substance 13 is immobilized on the capture substance 14. Further, the specific binding substance 13 recognizes and binds to the structure 12. In FIG. 5(b), the target molecule 11 has been extracted from the structure 12' after extraction.

The step of binding the capture substance to the structure can be performed at any time during the detection method of the present embodiment. For example, the step can be performed by bringing the structure and the capture substance into contact with each other in a sample tube before the step of introducing the structure into the well. Alternatively, binding can be performed by bringing the structure into contact with the capture substance after the capture substance is introduced into the well.

The capture substance is a substance capable of capturing the structure. Examples of the capture substance include, but are not limited to, a substance specifically binding to the target molecule (specific binding substance), which is immobilized on a solid phase, for example, particles. The capture substance may have one specific binding substance, or two or more, for example, three, four, or five specific binding substances. Alternatively, for example, when a virus is used as the structure, a cell to which the virus can be attached (that is, a cell having a virus receptor) can be used as the capture substance.

Examples of the specific binding substance include antibodies, antibody fragments, aptamers, and the like. Antibodies can be prepared, for example, by immunizing an animal such as a mouse or the like with a target molecule or a fragment of a target molecule as an antigen. Alternatively, for example, antibodies can be prepared by screening a phage library. Examples of the antibody fragment include Fab, F(ab')$_2$, Fab', single chain antibody (scFv), disulfide stabilized antibody (dsFv), dimeric V region fragment (Diabody), peptide including CDR, and the like. The antibody may be a monoclonal antibody or a polyclonal antibody. Alternatively, the antibody may be a commercially available antibody.

The particle is not specifically limited, and a polymer particle, magnetic particle, glass particle, and the like can be used. The particle is preferably subjected to a surface treatment in order to avoid nonspecific adsorption. Further, in order to immobilize the specific binding substance, it is preferred to use particles having a functional group such as a carboxyl group on the surface. More specifically, a product "Magnosphere LC300" manufactured by JSR Corporation or the like can be used.

The method of immobilizing the specific binding substance on the surface of the particle is not limited, and it is possible to use a method by physical adsorption, a method by chemical bonding, a method using avidin-biotin binding, a method of using a bond between protein G or protein A to an antibody, or the like. As the method by physical adsorption, there is a method of immobilizing a specific binding substance on the particle surface by hydrophobic interaction or electrostatic interaction. As the method by chemical bonding, there is a method using a crosslinking agent. For example, in the case where the surface of the particle has a hydroxyl group, the carboxyl group of the specific binding substance is allowed to react with a crosslinking agent to obtain an active ester, and then the hydroxyl group and the ester group are allowed to react, whereby the specific binding substance can be immobilized on the particle surface. It is also preferable to provide a spacer between the specific binding substance and the particle surface so as not to inhibit the recognition ability of the specific binding substance to recognize the target molecule.

In an embodiment of the present invention, the step of introducing the structure may be performed by introducing the capture substance into the wells of the well array. For example, a dispersion liquid of the structure bound to the capture substance to which the specific binding substance has been bound by the above method may be supplied into the flow path and introduced into the well.

Preferably, the capture substance and the structure are brought into contact with each other under a condition that 0 or 1 structure is captured by one capture substance. Furthermore, each well is preferably configured to accommodate 0 or 1 capture substance. Thus, digital measurement can be performed. That is, in the present embodiment, detection of the structure may be performed in units of one piece. In this case, the target molecule included in the structure is detected in units of one piece.

Further, in an embodiment of the present invention, a step of extracting the target molecule from the structure can be performed by a capture substance. In addition, in an embodiment of the present invention, the step of detecting the structure can be performed by detecting the specific binding substance of the capture substance.

Third Embodiment

A method for detecting a target molecule according to the third embodiment will be described. In the present embodiment, the step of extracting the target molecule from the structure in the method according to the first embodiment is performed by using a substance (extractant) that can act on the structure to extract the target molecule. The extractant may be any substance used to perform the above extraction step, and may be, for example, surfactants, antibiotics, osmotic pressure inducers, necrosis or apoptosis inducers, or the like used in the chemical techniques, or enzymes, viruses, phages, or the like used in the biological techniques. For example, when a cell is used as a structure, the cell can be infected with a virus as the extractant to lyse the cell, and the nucleic acid can be extracted as the target molecule.

The method according to the present embodiment includes a step of bringing the structure into contact with the extractant. The structure and the extractant may be brought into contact with each other in any order. For example, the structure and the extractant may be mixed prior to the step of introducing the structure into the well, and then the mixed solution can be supplied to be introduced into the well. In this case, the extraction conditions may be designed so that the target molecule is extracted from the structure in the well after the well is sealed by adjusting the mixing ratio between the structure and the extractant, or the like. Alternatively, a dispersion liquid of the structure may be supplied after the extractant is introduced into the well so that they are in contact with each other in the well.

After the well is sealed, the structure is disrupted due to the effect of the extractant in the well, and the target molecule is extracted. The extracted target molecule can be detected by the method described above.

Fourth Embodiment

A method for detecting a target molecule according to a fourth embodiment will be described. In the present embodiment, in the method according to the first embodiment, the first target molecule present on the surface of the structure, and the second target molecule present inside the structure are detected.

First, as in the first embodiment, the structures are introduced into the wells and the wells are sealed. Subsequently, the first target molecule is detected. The first target molecule can be detected by any method, and, for example, may be performed by using a specific binding substance to the first target molecule, and the specific binding substance may be bound to the first target molecule before the introduction into the wells or after the introduction into the wells.

Subsequently, the second target molecule is extracted in the well, and the extracted target molecule can be detected by the method described above.

The first target molecule and the second target molecule may be detected in sequence as described above or may be simultaneously detected.

EXAMPLES

The present invention will be hereinafter described in further detail based on examples. The present invention should not be limited to any of these examples.

In the present example, in order to manufacture a fluid device for an experiment, two resin members including a COP substrate and a COP cover member (with carbon black added for coloring, and a liquid supply port and a liquid discharge port provided) formed by injection molding were used. A well (micro compartment) formed in the substrate had a diameter of 5 μm, and had a volume such that signal detection by an invader reaction was possible in several minutes. The substrate was adhered to the cover member to form an internal space (flow path) of the fluid device having a height of 100 μm.

Example 1

(Study on Disruption of Phage and Extraction of Nucleic Acid from Phage)

An fl phage, which is a type of virus, (reagent name: *Escherichia coli* phage fl, National Institute of Technology and Evaluation, Model No. NBRC20010) (in which a base sequence of "SEQ ID NO: 1" is included as an encapsulated DNA (fl phage oligo)) (see Table 1) was used as a structure. A study was performed on the disruption of phage, and, detection of the target molecule, which was a nucleic acid, specifically, fl phage-encapsulated DNA, was performed. (Preparation of Nucleic Acid Detection Reagent)

In order to perform a digital Invader reaction, which is a type of ICA reaction, an Invader reaction reagent (ICA reaction reagent) was prepared as a nucleic acid detection reagent.

The Invader reaction reagent in Example 1 was prepared by using reagents shown in Table 1 to include 0.5 μm allele probe 1 ((fl phage) allele probe 1) (SEQ ID NO: 2), 1 μm Invader oligo 1 (SEQ ID NO: 3) (ICA oligo 1) (both from Fasmac Co., Ltd.), 4 μm FRET Cassette 1 (Alexa488-BHQ)

(SEQ ID NO: 4) (Japan Bio Services Co., Ltd.) (fluorescent substrate), 0.1 mg/mL FEN-1 (Flap endonuclease-1), 50 mM Tris-HCl (pH8.5), and 20 mM MgCl$_2$.

Note that the concentration of each component in the Invader reaction reagent is the final concentration in the Invader reaction reagent according to Example 1.

TABLE 1

| Reagent name | Base sequence (5' → 3') |
|---|---|
| fl phage oligo DNA (fl phage-encapsulated DNA) | ACGTTAAACAAAAAATCGTTTCTTATTTGGATTGG GATAAATAATATGGCTGTTTATTTTGTAACTGGCA AATTAGGCTCTGGAAAGACGCTCGTTAGCGTTGGT AAGATTCAGGATAAAATTGTAGCTGGGTGCAAAAT (SEQ ID NO: 1) |
| Allele probe 1 | CGCGCCGAGGGCCTAATTTGCCAGTTAC (SEQ ID NO: 2) |
| Invader oligo 1 (ICA oligo 1) | GCTAACGAGCGTCTTTCCAGAT (SEQ ID NO: 3) |
| FRET Cassette1 (Alexa488-BHQ) | XTTCTYAGCCGGTTTTCCGGCTGAGACCTCGGCGCG X: terminal amino group modified with Alexa488-NHS Y: BHQ1-dT phosphoramidite (SEQ ID NO: 4) |
| Allele probe 2 | CGCGCCGAGGCGCAGCTCATGCCC (SEQ ID NO: 5) |
| Invader oligo 2 (ICA oligo 2) | CCACCGTGCACTCATCAA (SEQ ID NO: 6) |

<Study on Disruption of Phage and Nucleic Acid Extraction Reaction>

It was studied whether the phage could be disrupted by a surfactant.

As a sample containing a surfactant, a solution (solution A) was prepared in a sample tube, by mixing a solution in which the above Invader reaction reagent and Bugbuster (manufactured by Merck Millipore Ltd.), which is a nucleic acid extraction reagent containing a surfactant were included at 1:1, and the above fl phage (1%). Then, the solution was stirred at room temperature for 15 minutes.

As a control experiment, a solution (solution B) was prepared in a sample tube, by mixing the above Invader reaction reagent and the above fl phage (1%) (sample that does not contain a surfactant). Then, the solution was stirred at room temperature for 15 minutes.

In this example and the following examples, the concentration of the fl phage is represented as a dilution ratio in which the concentration of the commercially available fl phage suspension is taken as 100%.

<Supply of Reaction Mixed Solution>

20 µL of the above solution A containing a surfactant was supplied into the fluid device, and introduced into the respective wells. Then, 150 µL of FC-40 (manufactured by Sigma) was supplied as a sealing solution to seal the respective wells. Thus, one or less fl phage per well was sealed in each welt.

Similarly, as a control experiment, 20 µL of the solution B that does not contain a surfactant was supplied into the fluid device, and introduced into the respective wells. Then, 150 µL of FC-40 (manufactured by Sigma) was supplied as a sealing solution to seal the respective wells.

<Nucleic Acid Detection Reaction>

The above fluid device was set on a hot plate and allowed to react at 66° C. for 15 minutes. As a result, recognition of phage-encapsulated DNA by allele probe and Invader oligo, cleavage of allele probe by FEN-1, binding of the released allele probe fragment to the FRET Cassette, and cleavage of FRET Cassette by FEN-1, and generation of fluorescence signal of Alexa488 occurred.

<Fluorescence Observation of Well>

After heating at 66° C. for 15 minutes, the fluorescence image of a fluorescence signal obtained by a nucleic acid detection reaction in the wells of the fluid device was acquired by using a 10× objective lens of a fluorescence microscope BZ-710 (KEYENCE Corporation). The exposure time was 3000 msec using a GFP fluorescence filter.

Figure 6A:
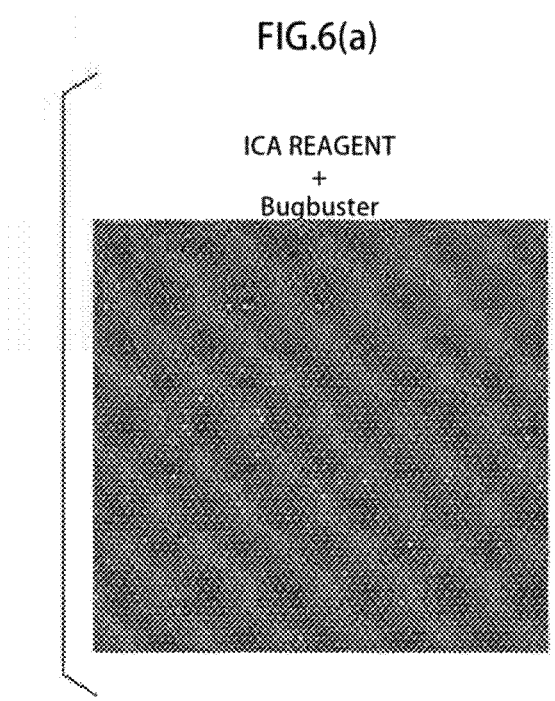
FIGS. 6(a) and 6(b) show results of fluorescence microscopic observation according to Example 1.
Figure 6B:
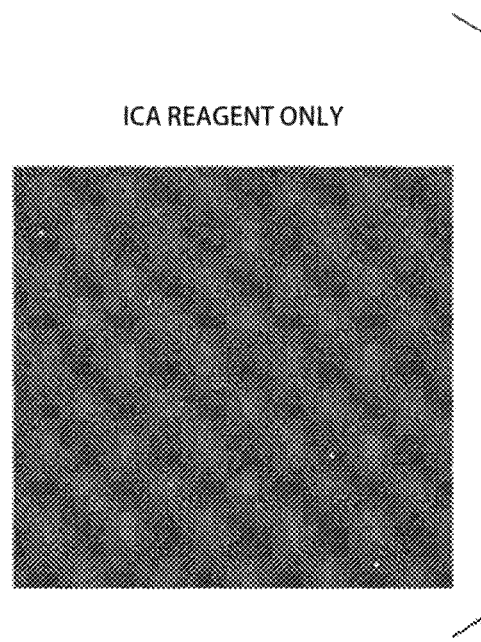

FIGS. 6(a) and 6(b) show the result of Example 1.

As shown in FIG. 6(a), when the solution A prepared by using a mixture solution in which the Invader reaction reagent (ICA reagent) and Bugbuster were mixed and the fl phage was supplied to the fluid device, a number of fluorescence signals derived from phage-encapsulated DNA, which were the target of detection, were observed in the wells of the fluid device.

On the other hand, as shown in FIG. 6(b), when the solution B prepared by using the Invader reaction reagent (ICA reagent) and fl phage without adding Bugbuster was supplied to the fluid device, fluorescence signals derived from phage-encapsulated DNA, which were the target of detection, were hardly observed in the wells of the fluid device.

According to the present example, the nucleic acid in the phage (fl phage oligo, fl phage-encapsulated DNA) was detected when Bugbuster was added, so it was suggested that the nucleic acid was extracted from the inside of the phage.

Based on this result, it was revealed that the phage was not disrupted by the Invader reaction reagent only, whereas the phage is disrupted when the reagent including a surfactant such as Bugbuster was used.

Further, it is considered that the disruption of the fl phage has started, though only partially, and extraction of the nucleic acid in the fl phage has started at the time when the solution (solution A) was prepared by mixing a solution in which the above Invader reaction reagent and Bugbuster, which is a nucleic acid extraction reagent containing a surfactant, were included at 1:1, and the above fl phage (1%), and stirred at room temperature for 15 minutes in a sample tube.

Example 2

(Study on Disruption of Phage in Wells of Fluid Device, Extraction of Nucleic Acid, and Detection of Nucleic Acid)

In this example, the disruption of phage was performed inside the fluid device, instead of introducing a measurement sample into the fluid device after disruption of the phage and extraction of the internal nucleic acid were performed in advance, and a study was performed on whether the nucleic acid in the phage can be detected inside the fluid device.

In this example, as in Example 1, an fl phage, which is a type of virus, (reagent name: *Escherichia coli* phage fl , National Institute of Technology and Evaluation, Model No. NBRC20010) (in which a base sequence of "SEQ ID NO: 1" is included as an encapsulated DNA) (see Table 1) was used as a structure.

In this example, a study was performed on the disruption of phage in the wells of the fluid device, and, detection of the target molecule, which was a nucleic acid, specifically, fl phage-encapsulated DNA, was performed.
(Preparation of Nucleic Acid Detection Reagent)

The Invader reaction reagent in Example 2 was prepared by using reagents shown in Table 1 to include 0.5 µm allele probe 1 ((SEQ ID NO: 2), 1 µm Invader oligo 1 (SEQ ID NO: 3) (ICA oligo 1) (both from Fasmac Co., Ltd.), 4 µm FRET Cassette 1 (Alexa488-BHQ) (SEQ ID NO: 4) (Japan Bio Services Co., Ltd.) (fluorescent substrate), 0.1 mg/mL FEN-1, 50 mM Tris-HCl (pH8.5), 20 mM $MgCl_2$, and 0.05% Tween20. Note that the concentration of each component in these Invader reaction reagents is the final concentration in the Invader reaction reagent according to Example 2.

A solution (solution C) was prepared by mixing a solution in which the above Invader reaction reagent and Bugbuster (manufactured by Merck Millipore Ltd.), which is a nucleic acid extraction reagent containing a surfactant, were included at 1:1.
<Supply of Mixture Solution>

20 µL of a solution obtained by mixing a suspension of the above fl phage as a virus sample and the solution C, in which the above Invader reaction reagent and Bugbuster were mixed, was supplied into the fluid device to be introduced into the respective wells.

In addition, the mixture solution of the fl phage suspension and the solution C was supplied at four types of fl phage concentrations so that the final concentration of the fl phage in the fluid device became 0% (fl phage was not added), 0.1%, 0.5%, and 1.0%. As in the above Example 1, the concentration of the fl phage is represented as a dilution ratio in which the concentration of the commercially available fl phage suspension is taken as 100%.

Further, the concentration of the components in the solution C was adjusted such that the disruption of the fl phage does not occur immediately after the solution is mixed with the fl phage suspension, but occurs when a nucleic acid extraction reaction, which will be described later, is performed after the solution is introduced in the wells.

Then, 150 µL of FC-40 (manufactured by Sigma) was supplied as a sealing solution to seal the respective wells.
<Nucleic Acid Extraction Reaction>

The above fluid device was set on a hot plate and allowed to react at 66° C. for 30 minutes. Thus, the capsid structure of the fl phage was disrupted and DNA was extracted in the sealed wells.
<Nucleic Acid Detection Reaction>

As the fluid device was heated, reactions of the Invader method proceeded as in Example 1, and a fluorescence signal of Alexa488 was finally generated.
<Fluorescence Observation of Well>

After heating at 66° C. for 30 minutes, the fluorescence image of a fluorescence signal obtained by a nucleic acid detection reaction in the wells of the fluid device was acquired by using a 10x objective lens of a fluorescence microscope BZ-710 (KEYENCE Corporation). The exposure time was 3000 msec using a GFP fluorescence filter.

Figure 7:
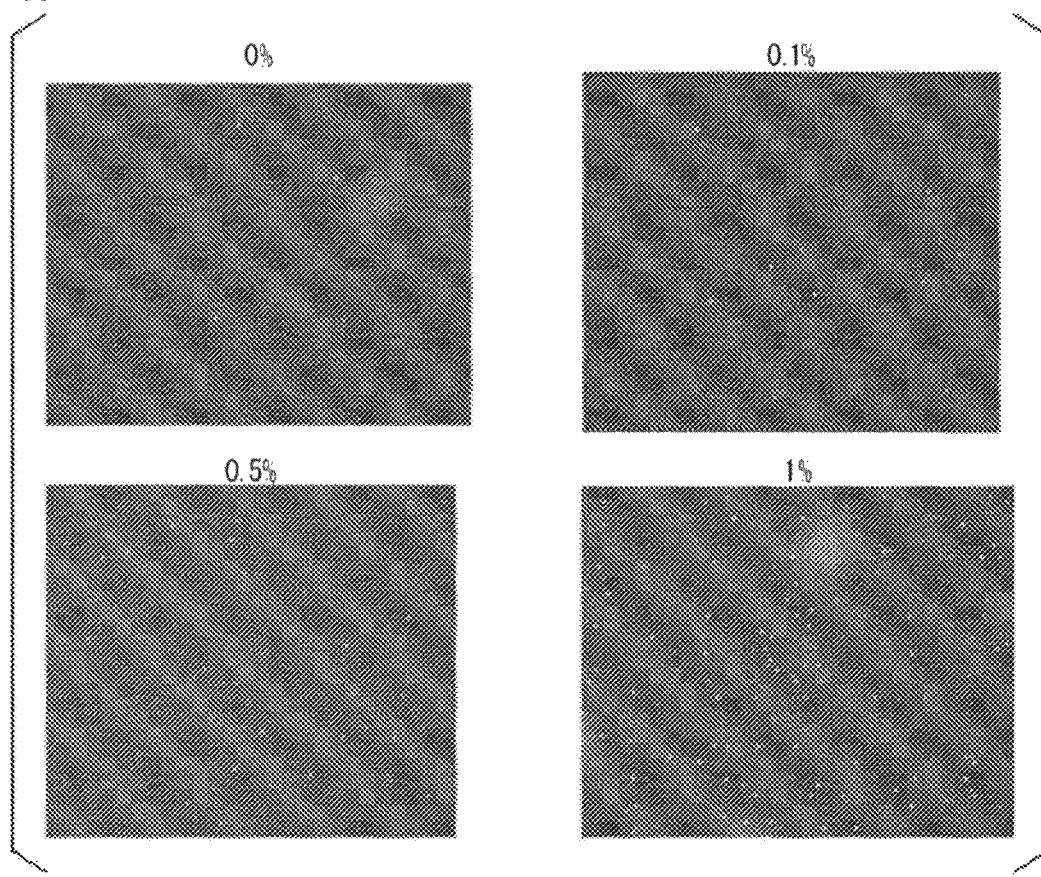
FIG. 7 shows results of fluorescence microscopic observation according to Example 2.
Figure 8:
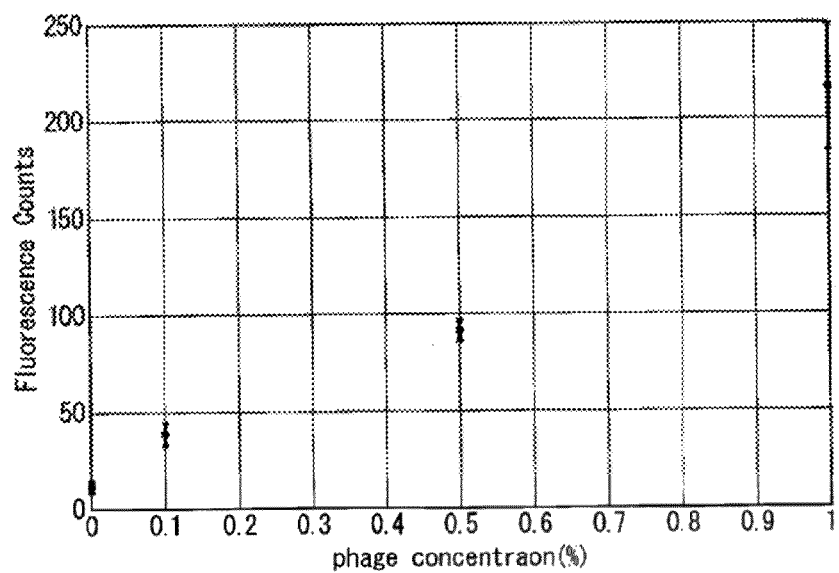
FIG. 8 is a graph showing the number of wells in which fluorescence is observed with respect to a phage concentration according to Example 2.

FIGS. 7 and 8 show the result of Example 2.

As shown in FIGS. 7 and 8, in the wells in which the fl phage-encapsulating DNA, which is the target molecule, was present, a fluorescence signal derived from the target molecule was observed.

Further, as shown in the fluorescence image in FIG. 7 and the graph in FIG. 8, the number of wells in which fluorescence was observed increased depending on the concentration of the fl phage.

According to this example, it was considered that the fl phage was introduced into the wells, and the nucleic acid in the fl phage was extracted depending on the concentration of the fl phage.

In other words, according to the above method, the nucleic acid as the target molecule was accurately detected by reducing a loss of DNA in the fl phage.

Example 3

(Binding of Beads to Phage, Introduction of Bead-bound Phage into Wells, and Detection of Nucleic Acid in Virus (Phage))

An fl phage, which is a type of virus, (reagent name: *Escherichia coli* phage fl, National Institute of Technology and Evaluation, Model No. NBRC20010) (in which a base sequence of "SEQ ID NO: 1" is included as an encapsulated DNA) (see Table 1) was used as a structure to detect a nucleic acid in a virus as a target molecule. Further, in introduction of the structure into the wells, magnetic beads having an antibody as a specific binding substance were used as a capture substance.
<Preparation of Nucleic Acid Detection Reagent>

The Invader reaction reagent in Example 3 was prepared by using reagents shown in Table 1 to include 0.5 µm allele probe 1 ((fl phage) Allele probe 1 (SEQ ID NO: 2), 1 µm Invader oligo 1 (SEQ ID NO: 3) (ICA oligo 1) (both from Fasmac Co., Ltd.), 4 µm FRET Cassette 1 (Alexa488-BHQ) (SEQ ID NO: 4) (Japan Bio Services Co., Ltd.) (fluorescent substrate), 0.1 mg/mL FEN-1, 50 mM Tris-HCl (pH8.5), 20 mM $MgCl_2$, and 0.05% Tween20. Note that the concentration of each component in these Invader reaction reagents is the final concentration in the Invader reaction reagent according to Example 3.

A solution (solution D) was prepared by mixing a solution in which the above Invader reaction reagent and Bugbuster (manufactured by Merck Millipore Ltd.), which is a nucleic acid extraction reagent containing a surfactant, were included at 1:1.
<Preparation of Antibody-Immobilized Magnetic Beads>

In order to immobilize the phage antibody on magnetic beads, an anti-fl phage antibody (type "Anti-M-13 Phage Coat Protein," Funakoshi. Co., Ltd.) was added to a carboxyl group-modified magnetic bead (Magnosphere, LC 300, JSR) solution and mixed to 100 µL, the mixture was rotated with a rotator and the reaction was allowed to proceed for 30 minutes, then a condensing agent EDC was further added, and the reaction was carried out for 3 hours to immobilize the antibody on the carboxyl magnetic beads.

In order to remove unreacted antibody and reagent after the reaction, antibody-immobilized carboxyl magnetic beads were magnetically captured using a magnetic stand. Subsequently, washing was repeatedly three times by using PBS-T (0.1% Tween 20-containing PBS) to prepare antibody-immobilized carboxylic magnetic beads. Thus, a capture substance having a specific binding substance was prepared.
<Reaction of Sample and Antibody-immobilized Magnetic Beads>

The fl phage (0% or 1%) as a structure, and 100 µg/mL antibody-immobilized carboxylic magnetic beads as a capture substance having a specific binding substance were mixed so that the total amount of immobilized carboxylic magnetic beads was 100 µL, and the mixture was allowed to react at room temperature for 1 hour on a rotator to form a composite.

After the reaction, the magnetic beads obtained were magnetically collected using a magnetic stand, removal of the supernatant and addition of 0.1% Tween-containing PBS (PBS-T) were performed three times for washing, and finally the supernatant was removed to obtain a complex.

The composite was formed when the anti-fl phage antibody immobilized on the beads recognized and bound to a coat protein on the fl phage surface. The obtained complex was then washed and diluted with PBS to prepare a reaction mixture.

<Supply of Reaction Mixed Solution>

20 μL of a solution obtained by mixing the above reaction mixture (fl phage 0%, 1% collected by beads) and the solution D, in which the Invader reaction reagent and Bugbuster were included at 1:1, was supplied into the fluid device to be introduced into the respective wells. Then, 150 μL of FC-40 (manufactured by Sigma) was supplied as a sealing solution to seal the respective wells. Thus, when the fl phage collected by the beads was included, one or less fl phage per well was sealed in each well.

<Observation of Well>

After the detection reaction, the bright field image of the fluid device was imaged by using a 10× objective lens of a microscope BZ-710. In the well in which the beads were introduced, a black color is observed in the bright field image as shown in the right image of FIG. 9.

<Nucleic Acid Extraction Reaction>

The above fluid device was set on a hot plate and allowed to react at 66° C. for 15 minutes. Thus, the capsid structure of the fl phage was disrupted and DNA was extracted in the sealed wells.

<Nucleic Acid Detection Reaction>

As the fluid device was heated at 66° C. for 15 minutes, reactions of the Invader method proceeded as in Example 1, and a fluorescence signal of Alexa488 was finally generated.

<Fluorescence Observation of Well>

After heating at 66° C. for 15 minutes, the fluorescence image of a fluorescence signal obtained by a nucleic acid detection reaction in the wells of the fluid device was acquired by using a 10× objective lens of a fluorescence microscope BZ-710 (KEYENCE Corporation). The exposure time was 3000 msec using a GFP fluorescence filter.

Figure 9:
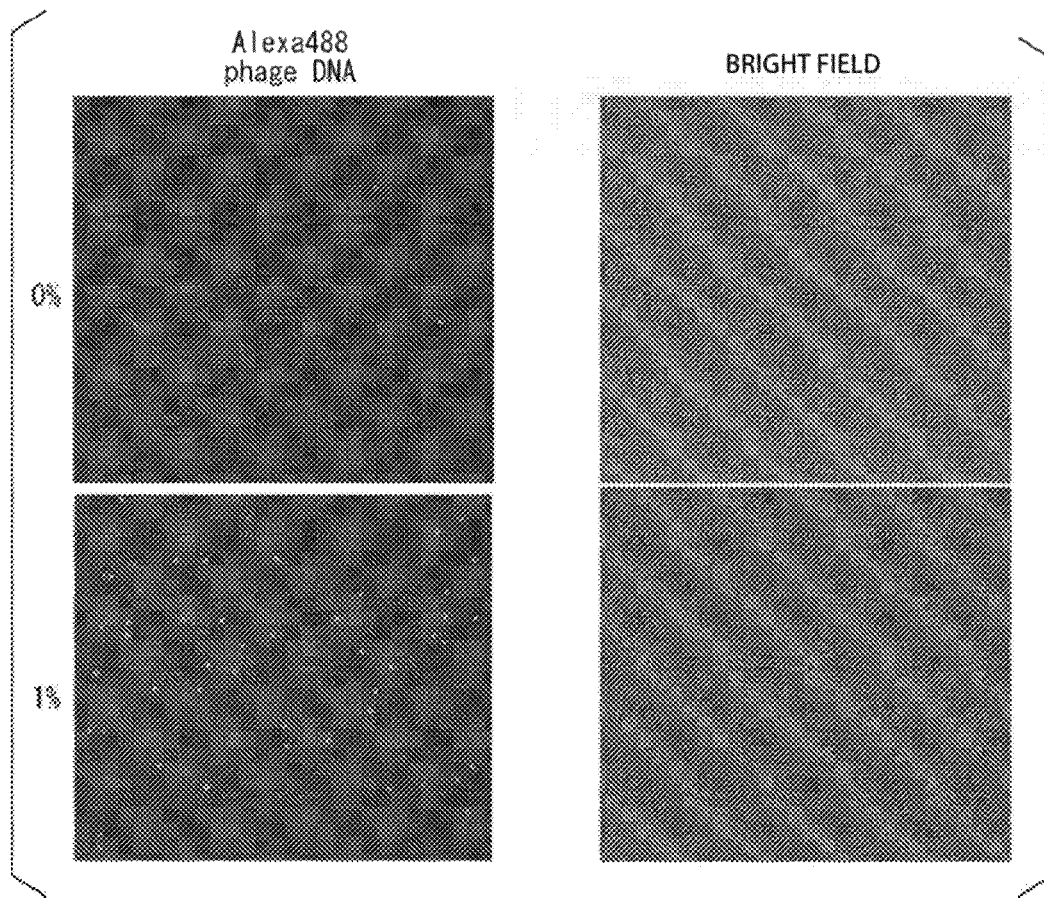
FIG. 9 shows results of fluorescence microscopic observation according to Example 3.

FIG. 9 shows the result of Example 3.

As shown in the right image of FIG. 9 (bright field image), the well displayed in black was the well into which the beads were introduced.

Further, as shown in the 1% fluorescence image of the left image in FIG. 9, a fluorescence signal derived from the target molecule was observed in the wells in which the fl phage-encapsulating DNA, which is the target molecule, was present.

According to the above method, the nucleic acid as the target molecule was accurately detected by reducing a loss of DNA in the fl phage. Further, magnetic beads having an antibody as a specific binding substance were used as a capture substance, so the structure can be efficiently introduced into the well.

Further, the anti-fl phage antibody recognizes a coat protein on the fl phage surface. Therefore, according to the above technique, the target molecule on the surface of the fl phage, in addition to the target molecule contained in the fl phage, was detected by using the capture substance.

Example 4

(Study on Various Techniques for Disrupting Phage)

In this example, whether phage disruption was possible or not was studied by using various techniques.

An fl phage, which is a type of virus, (reagent name: Escherichia coli phage fl, National Institute of Technology and Evaluation, Model No. NBRC20010) (in which a base sequence of "SEQ ID NO: 1" is included as an encapsulated DNA) (see Table 1) was used as a structure. A study was performed on the disruption of phage by using various techniques, and, detection of the target molecule, which was a nucleic acid, specifically, fl phage-encapsulated DNA, was performed.

(Preparation of Nucleic Acid Detection Reagent)

In order to perform a digital Invader reaction, which is a type of ICA reaction, an Invader reaction reagent (ICA reaction reagent) was prepared as a nucleic acid detection reagent.

The Invader reaction reagent in Example 4 was prepared by using reagents shown in Table 1 to include 0.5 μm allele probe 1 ((fl phage) allele probe 1) (SEQ ID NO: 2), 1 μm Invader oligo 1 (SEQ ID NO: 3) (ICA oligo 1) (both from Fasmac Co., Ltd.), 2 μm FRET Cassette 1 (Alexa488-BHQ) (SEQ ID NO: 4) (Japan Bio Services Co., Ltd.) (fluorescent substrate), 0.1 mg/mL FEN-1 (Flap endonuclease-1), 50 mM MOPS (3-morpholinopropanesulfonic acid buffer) (pH7.9), and 20 mM MgCl$_2$.

Note that the concentration of each component in these Invader reaction reagents is the final concentration in the Invader reaction reagent according to Example 4.

<Study on Phage Disruption by Various Techniques and Study on Nucleic Acid Extraction Reaction>

A study on phage disruption was performed under the conditions below.

Sample 1: Sonication (probe type ultrasonic wave) was applied to the phage (10%) for 1 minute.

Sample 2: Bugbuster (50%) was applied to the phage (10%), and the mixture was stirred at 37° C. for 30 minutes.

Sample 3: The phage (10%) was heated at 70° C. for 30 minutes.

Sample 4: Bugbuster (50%) was applied to the phage (10%), and the mixture was stirred at 70° C. for 30 minutes.

Then, the above Invader reaction reagent and the samples 1 to 4 were mixed in the sample tube to prepare the solutions (samples 1A to 4A) having a phage concentration of 1%, and a volume of 10 μL.

As negative controls, the Invader reaction reagent only (sample 5A) and a mixed solution of the Invader reaction reagent and the phage (sample 6A) were prepared and evaluated.

Further, as a positive control, a solution obtained by adding a phage-derived nucleic acid (phage oligo) (SEQ ID NO: 1) 30 pM extracted from the phage in advance to the Invader reaction reagent (sample 7A) was prepared and evaluated.

These sample solutions of the samples 1A to 7A were processed with a real time PCR device Light Cycler (manufactured by Roche Diagnostics K.K.) at 66° C. for 60 minutes.

Figure 10:
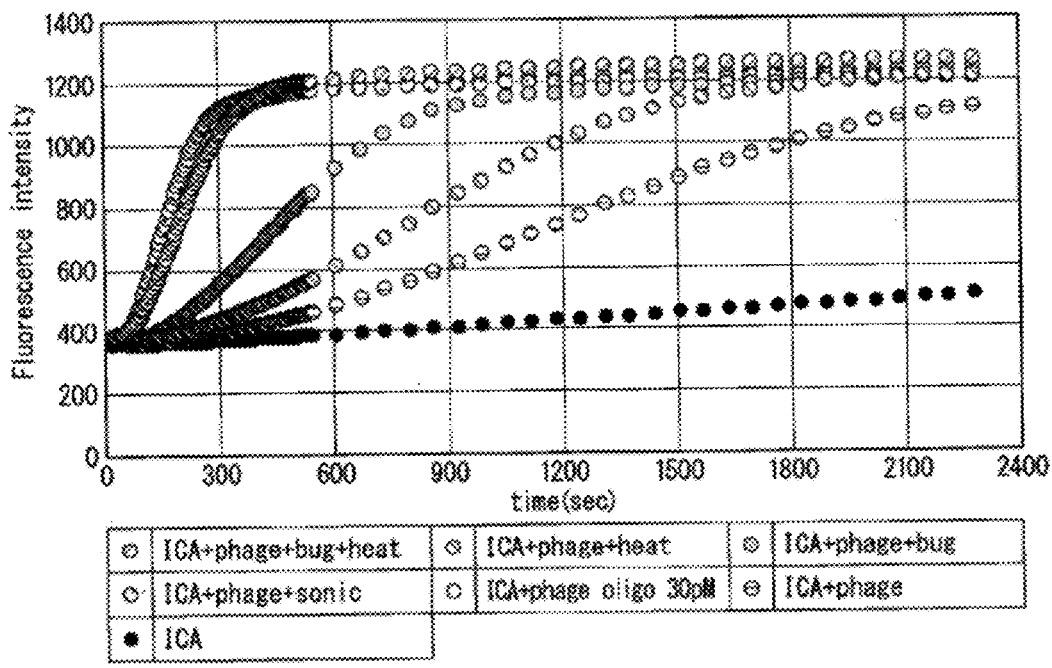
FIG. 10 is a graph showing a change in fluorescence intensity with respect to time, in a study on detection of a nucleic acid in a phage by various techniques of disrupting the phage according to Example 4.
Figure 11:
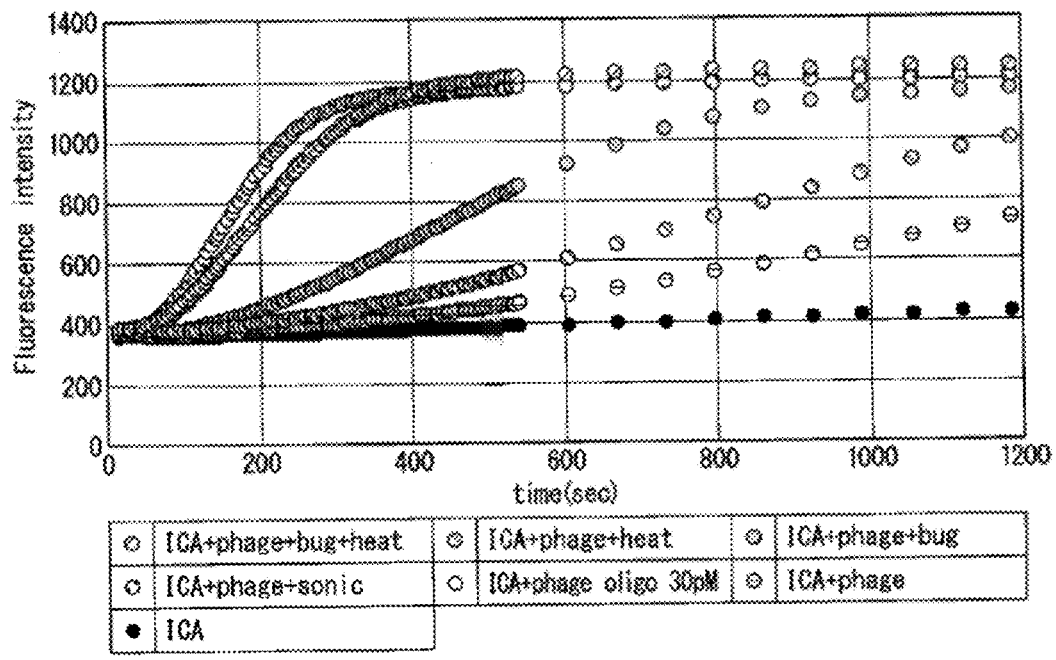
FIG. 11 is an enlarged view of FIG. 10, which shows a change in fluorescence intensity with respect to time, in a study on detection of a nucleic acid in a phage by various techniques of disrupting the phage according to Example 4.

FIGS. 10 and 11 show the result of Example 4.

FIG. 11 is an enlarged view up to around 1200 seconds in FIG. 10.

In the graphs of FIGS. 10 and 11, the horizontal axis represents the processing time (seconds), and the vertical axis represents the fluorescence intensity.

The items shown in FIGS. 10 and 11 correspond to the sample numbers as follows.

Sample 1A: ICA+phage+sonic
Sample 2A: ICA+phage+bug
Sample 3A: ICA+phage+heat
Sample 4A: ICA+phage+bug+heat
Sample 5A: ICA
Sample 6A: ICA+phage
Sample 7A: ICA+phage+phage oligo 30 pM In each of the sample IA subjected to sonication, the sample 2A obtained by adding Bugbuster containing a surfactant to the phage, the sample 3A obtained by applying a heat treatment to the phage at 70° C., the sample 4A obtained by adding Bugbuster containing a surfactant to the phage and applying a heat treatment to the phage at 70° C. for 30 minutes, and the sample 7A which is a positive control, the fluorescence intensity was increased from a stage as short as 300 or 600 seconds into the treatment time.

In the sample IA obtained by applying sonication to the phage, and the sample 4A obtained by adding Bugbuster containing a surfactant to the phage and applying a heat treatment at 70° C., an increase in fluorescence intensity in a particularly short time was observed.

In the sample 5A, in which only the Invader reaction reagent was supplied to the Light Cycler as a negative control, an increase in fluorescence intensity was hardly observed.

Since the samples were processed by using the Light Cycler at 66° C., an increase in fluorescence intensity with time was also observed in the sample 6A (ICA+phage). However, the increase was gradual compared with the samples 1A to 4A.

In the samples 1A to 4A in which the phases were disrupted by various techniques, an increase in fluorescence intensity in a short time was observed compared with the samples 5A and 6A.

From these results, it was found that, for example, a plurality of techniques such as sonication and heating in addition to application of a surfactant, and a combination of a plurality of techniques were effective.

According to the present example, it was found that phage lysis and extraction of nucleic acid from the phage can be performed in a short time by combining the plurality of techniques described above.

Example 5

(Detection of Nucleic Acid in Virus, Detection of Internal Nucleic Acid by Bacteriolysis of *E. coli*)

In the present example, a study was performed on extraction of a nucleic acid derived from the phage by using bacteriolysis using phage and *E. coli*.

An fl phage, which is a type of virus, (reagent name: *Escherichia coli* phage fl, National Institute of Technology and Evaluation, Model No. NBRC20010) (in which a base sequence of "SEQ ID NO: 1" is included as an encapsulated DNA) (see Table 1) was used as a structure to detect a nucleic acid in a virus. Further, for extraction of a nucleic acid in a virus, which is a target molecule, a biological technique was used in which *Escherichia coli* (*E. coli*) (National Institute of Technology and Evaluation, Model No. NBRC13965) was used as a lipid bilayer donor.

<Preparation of Mixed Solution of Sample and Lipid Bilayer Donor>

As a virus sample, a reconstituted aqueous solution of an fl phage (NBRC20010) of a final concentration 1% and a reconstituted aqueous solution of *E. coli* (NBRC13965) of a final concentration 1% were mixed so that the total volume was 100 µL.

The fl phage was bound to a virus receptor present on the cell surface of *E. coli* to form a composite of the fl phage and *E. coli*.

The final concentration of the fl phage and the final concentration of *E. coli* were the final concentration in the fluid device.

(Preparation of Nucleic Acid Detection Reagent)

In order to perform a digital Invader reaction, which is a type of ICA reaction, an Invader reaction reagent (ICA reaction reagent) was prepared as a nucleic acid detection reagent.

The Invader reaction reagent in Example 5 was prepared by using reagents shown in Table 1 to include 0.5 µm allele probe 1 ((fl phage) allele probe 1) (SEQ ID NO: 2), 1 µm Invader oligo 1 (SEQ ID NO: 3) (ICA oligo 1) (both from Fasmac Co., Ltd.), 4 µm FRET Cassette 1 (Alexa488-BHQ) (SEQ ID NO: 4) (Japan Bio Services Co., Ltd.) (fluorescent substrate), 0.1 mg/mL. FEN-1, 50 mM Tris-HCl (pH8.5), 20 mM $MgCl_2$, and 0.05% Tween20.

Note that the concentration of each component in these Invader reaction reagents is the final concentration in the Invader reaction reagent in the fluid device according to Example 5.

<Supply of Mixture Solution>

20 µL of a solution obtained by mixing the above solution (mixed solution of the fl phage and *E. coli*) and the above Invader reaction reagent at 1:1 was supplied into the fluid device to be introduced into the respective wells. Then, 150 µL of FC-40 (manufactured by Sigma) was supplied as a sealing solution to seal the respective wells. Thus, one or less fl phage per well was sealed in each well.

After the sealing of wells, the fluid device was allowed to stand at room temperature for 60 minutes.

Further, as a negative control, the same operation was performed for a solution that uses only the fl phage without using *E. coli*, instead of the reaction mixture (reaction mixture of fl phage and *E. coli*).

That is, 20 µL of a solution obtained by mixing the fl phage and the above Invader reaction reagent at 1:1 was supplied into the fluid device to be introduced into the respective wells. Then, 150 µL of FC-40 (manufactured by Sigma) was supplied as a sealing solution to seal the respective wells.

<Nucleic Acid Extraction Reaction, Nucleic Acid Detection Reaction>

When the wells were sealed and allowed to react for 60 minutes, the fl phage as a structure recognized and bound to the surface membrane structure (protein, lipid bilayer) of *E. coli*, thereby allowing the DNA as a target molecule to be introduced from the fl phage into *E. coli*. That is, a composite of fl phage and *E. coli* was gradually formed during the reaction for 60 minutes. In addition, the DNA was replicated in *E. coli* to generate a phage. The fl phage generated in the bacterial cell disrupted the *E. coli*, and the injected and replicated DNA was released.

Further, the fluid device was allowed to react on a hot plate at 66° C. for 30 minutes. Accordingly, as the released fl phage DNA was recognized, reactions of the Invader method proceeded as in Example 1, and a fluorescence signal of Alexa488 was finally generated.

<Fluorescence Observation of Well>

After the fluid device was heated at 66° C. for 30 minutes as described above, the fluorescence image of a fluorescence signal obtained by a nucleic acid detection reaction in the wells of the fluid device was acquired by using a 10× objective lens of a fluorescence microscope BZ-710 (KEYENCE Corporation). The exposure time was 3000 msec using a GFP fluorescence filter.

Figure 12:
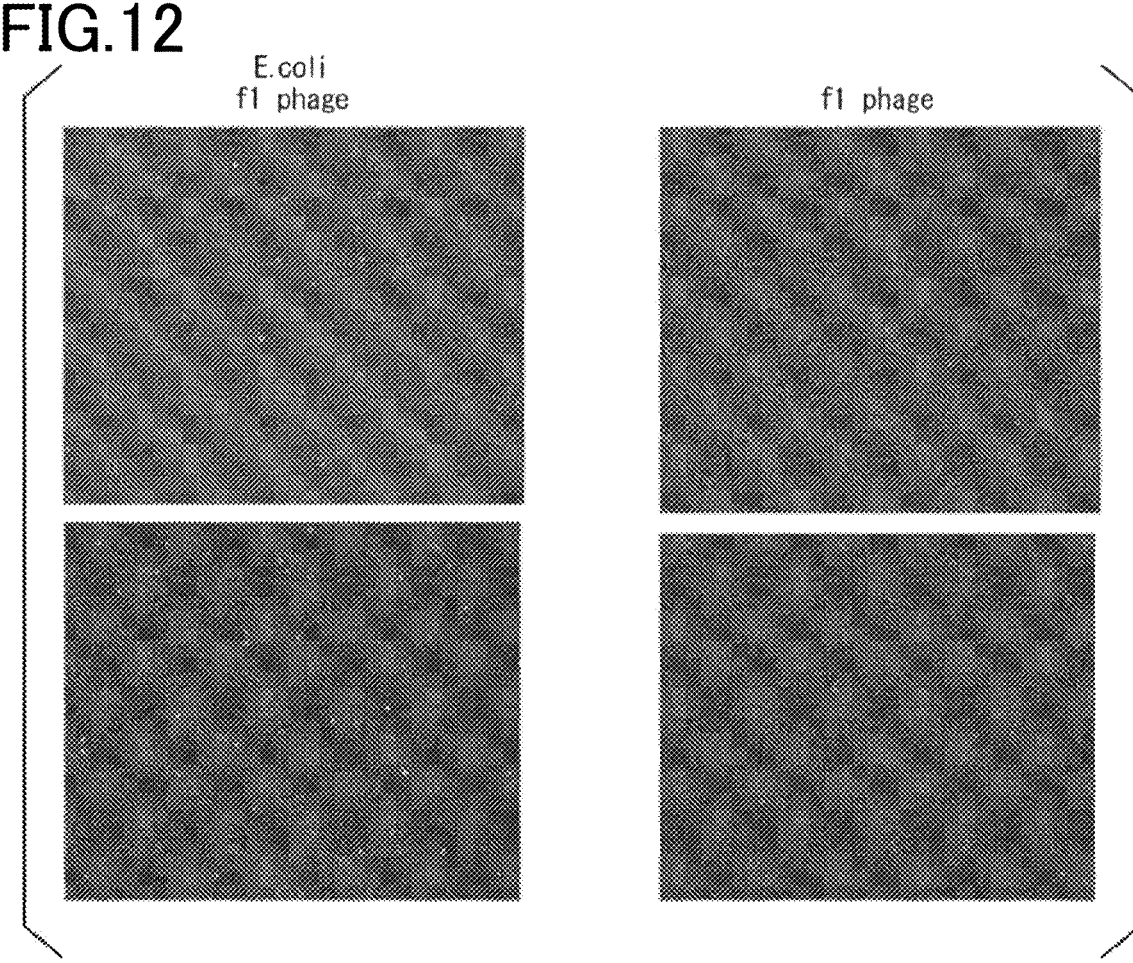
FIG. 12 shows results of fluorescence microscopic observation according to Example 5.

FIG. 12 shows the result of acquisition of fluorescence images according to Example 5.

As shown in the left image in FIG. 12, in the well in which the fl phage and *E. coli* were present, a fluorescence signal derived from the target molecule was observed.

As shown in the fluorescence image of FIG. 12, when the fl phage was infected with *E. coli* and introduced into the fluid device (left image in FIG. 12), a larger number of DNA were detected compared with a case where only the fl phage was introduced into the fluid device (right image in FIG. 12).

This result seems to indicate that a large number of fluorescence signals derived from the target molecule were observed since the fl phage was infected with *E. coli*, and the DNA derived from the fl phage was amplified in *E. coli*, which finally causes bacteriolysis of *E. coli* to thereby release the fl phage DNA, which is a target molecule.

Further, as shown in the right image in FIG. 12, a small number of fluorescence signals were observed when only the fl phage was introduced into the fluid device without adding *E. coli*. In the example in which *E. coli* was not added, it seems that the DNA was slightly released into the wells due to the effect of heating and Tween20, which was a surfactant contained in the buffer.

According to the above method, the nucleic acid as the target molecule was accurately detected by reducing a loss of DNA in the fl phage. Further, by using *E. coli* having a lipid bilayer, DNA as a target molecule was extracted from the virus as a structure in the well.

In addition, it was also found that, even if the object has a hard membrane as a phage, detection of DNA from the phage can be easily performed by transferring the DNA to another substance (for example, *E. coli*) and heating the substance.

Example 6

(Intracellular Nucleic Acid Detection 1)

Detection of a target molecule was performed by using human colon adenocarcinoma cells HT29 as a structure. The target molecule was a nucleic acid, specifically, a region including a single nucleotide polymorphism (wild type) of EGFR (epidermal growth factor receptor) gene, which is DNA.

<PKH Staining of HT29 Cell>

In order to confirm the introduction of HT29 cells into the fluid device, PKH-stained HT29 cells were prepared.

The PKH staining of HT29 cells was performed in the following procedure.

HT29 cultured cells were removed and a suspension was prepared. Further, the suspension was centrifuged at 3500 rpm for 1 minute to collect the cells. Subsequently, a sufficient amount of Diluent C reagent was added to the collected cells. A PKH solution was added to the cells to which Diluent C reagent had been added, and the mixture was allowed to stand at room temperature for 10 minutes.

Then, the cell suspension to which the PKH solution was added was centrifuged at 3500 rpm for 1 minute to collect the PKH-stained cells, which in turn were resuspended in DMEM medium solution.

The PKH-stained HT29 cells resuspended in the DMEM medium solution were mixed with the Invader reaction reagent, described later, and used for introduction into the fluid device.

Further, cells obtained by PKH-staining of HT29 cells were prepared so that the number of cells to be introduced into the fluid device becomes $5.16 \times 10^5$ cell/mL.

<Preparation of Nucleic Acid Detection Reagent>

In order to perform a digital Invader reaction, which is a type of ICA reaction, an Invader reaction reagent was prepared as a nucleic acid detection reagent. The Invader reaction reagent in this example was prepared by using reagents shown in Table 1 to include 0.5 μm allele probe 2 (SEQ ID NO: 5), 1 μm Invader oligo 2 (SEQ ID NO: 6) (ICA oligo 2) (both from Fasmac Co., Ltd.), 4 μm FRET Cassette 1 (Alexa488-BHQ) (Japan Bio Services Co., Ltd.) (fluorescent substance) (SEQ ID NO: 4), 0.1 mg/mL FEN-1, 50 mM Tris-HCl (pH8.5), 20 mM $MgCl_2$, and 0.05% Tween20. Note that the concentration of each component in these Invader reaction reagents is the final concentration in the Invader reaction reagent according to Example 5.

<Supply of Reaction Mixed Solution>

Figure 14:
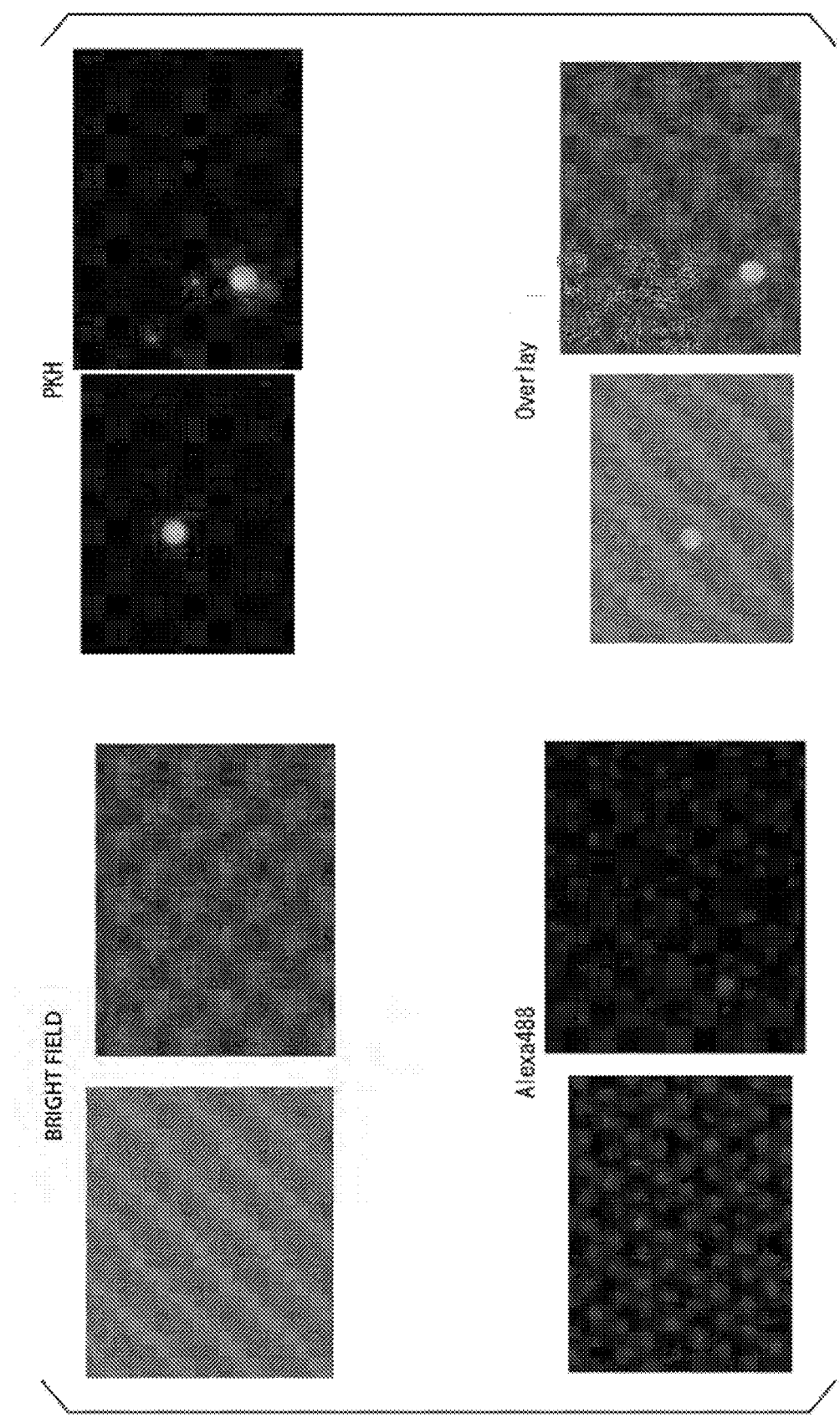
FIG. 14 shows results of fluorescence microscopic observation according to Example 6.

204 of a solution (number of cells: $5.16 \times 10^5$ cell/mL) obtained by mixing PKH-stained human colon adenocarcinoma cells HT29 and the above Invader reaction reagent was supplied into the fluid device to be introduced into the respective wells. Then, 150 μL of FC-40 (manufactured by Sigma) was supplied as a sealing solution to seal the respective wells (FIGS. 14 and 15). Thus, one or less HT29 cell per well was sealed in each well.

Figure 13:
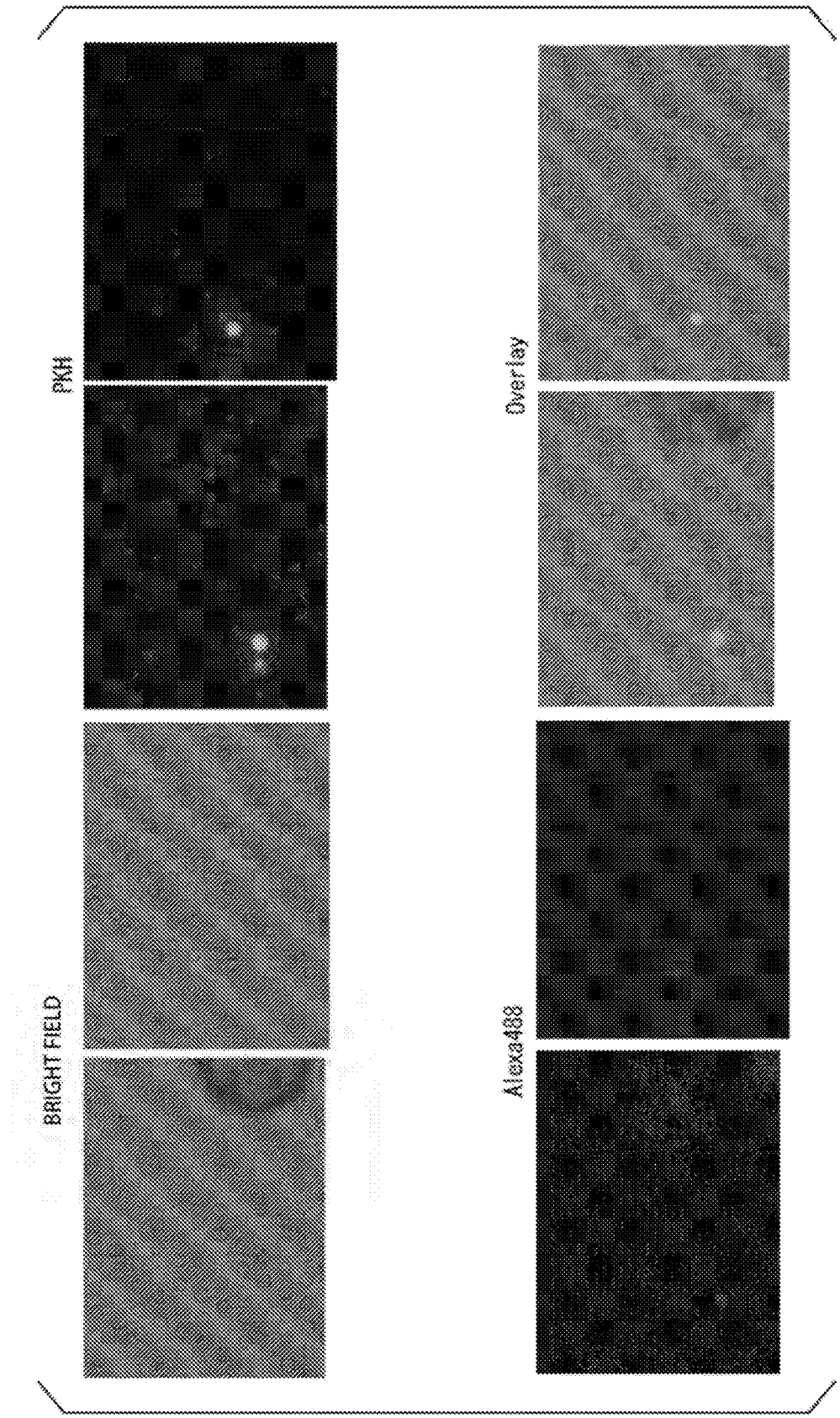
FIG. 13 shows results of fluorescence microscopic observation according to Example 6.

Further, a control experiment was performed in which a solution of human colon adenocarcinoma cells HT29 stained with NCH under the same conditions except that the Invader reaction reagent was not added (number of cells: $5.16 \times 10^5$ cell/mL) was supplied into the fluid device so that the HT29 cells were introduced into the wells (FIG. 13).

<Nucleic Acid Extraction Reaction>

The above fluid device was set on a hot plate and allowed to react at 66° C. for 15 minutes. Thus, the cell membrane structure of HT29 cells was disrupted and genomic DNA was extracted in the sealed wells.

<Nucleic Acid Detection Reaction>

The above fluid device after extraction reaction was set on a hot plate, and allowed to react at 66° C. for 15 minutes. As a result, recognition of EGFR gene region by allele probe and Invader oligo, cleavage of allele probe by FEN-1, binding of the released allele probe fragment to the FRET Cassette, and cleavage of FRET Cassette by FEN-1, and generation of fluorescence signal of Alexa488 occurred.

As a control experiment, the case where the fluid device was not heated at 66° C. for 15 minutes was also studied (FIG. 14).

<Fluorescence Observation of Well and Bright Field Observation>

After heating at 66° C. for 15 minutes, the fluorescence image of a fluorescence signal obtained by a nucleic acid detection reaction in the wells of the fluid device was acquired by using a 10× objective lens of a fluorescence microscope BZ-710 (KEYENCE Corporation).

The exposure time was 3000 msec using a GFP fluorescence filter in fluorescence observation of Alexa488, and 2000 msec using a Texas Red fluorescence filter in fluorescence observation of PKH.

Further, after the sealing of the wells, the bright field image was also imaged by using a 10× objective lens of a microscope BZ-710.

FIGS. 13 to 15 show the result of Example 6.

FIG. 13 is a fluorescence image of PKH-stained HT29 cells in the example in which no Invader reaction reagent was added.

As shown in FIG. 13, PKH staining revealed the cells introduced into the wells.

FIG. 14 is a fluorescence image of a fluid device before heating (heating at 66° C. for 15 minutes was not performed), into which a solution obtained by mixing PKH-stained human colon adenocarcinoma cells HT29 and the above Invader reaction reagent was introduced. In the fluorescence image, only PKH-derived fluorescence was detected.

FIG. 15 is a fluorescence image of a fluid device after heating, into which a solution obtained by mixing PKH-stained human colon adenocarcinoma cells HT29 and the above Invader reaction reagent was introduced. In the fluorescence image, both PKH-derived fluorescence and Alexa488 fluorescence were detected.

As shown in FIG. 13, PKH-staining of HT29 cells revealed that the HT29 cells were present in the wells of the fluid device.

Further, fluorescence of Alexa488 can be detected when DNA present in the HT29 cell migrates into the solution.

Accordingly, as shown in FIG. 15, the detection of Alexa488 indicated that the cell membrane of HT29 cells was disrupted.

In this example, the fluorescence image of PICH and fluorescence image of Alexa488 are overlaid (overlay images in FIGS. 13 to 15), and only PKH was detected in the case where no Invader reaction reagent containing a surfactant was added (FIG. 13) and the case where the Invader reaction reagent containing a surfactant was added before the device was heated (FIG. 14).

However, as shown in FIG. 15, after heating, fluorescence of Alexa488 was detected in the same well as that in which PKH was detected.

Therefore, it seems that, in the example of FIG. 15 in which a surfactant was added and heating was applied, the Invader reaction proceeded in the wells in which HT29 cells were present, and DNA in the HT29 cells was detected.

From these results, it was found that, according to the present example, the internal nucleic acid can be detected by disrupting the HT29 cells by applying heat to thereby extract the nucleic acid from the cells present in the wells.

Thus, a fluorescence signal derived from the target molecule was observed in the wells in which the EGFR gene region containing a single nucleotide polymorphism, which is the target molecule, was present.

It was found that, according to the above method, the nucleic acid as the target molecule was accurately detected by reducing a loss of genomic DNA in the HT29 cells.

The present application addresses the following. Digital measurement may be performed by extracting a target molecule from a structure containing a target molecule (for example, a cell as a structure containing a nucleic acid as a target molecule, which will be described later), supplying and distributing the extracted target molecule, and generating a signal when the target molecule is present in a microdroplet to thereby detect the presence of the target molecule. However, in extraction of a target molecule from the structure, some of the target molecules may be lost and their quantity may be reduced. Further, as described in PTL 1, in the detection method in which a sample is introduced into each well of a micro array by using a flow path and oil, the target molecule in the sample may be left in the flow path without being distributed to respective wells, and expelled by the oil, leading to a decrease in the number of target molecules.

As a result, the detection accuracy of the target molecule may be reduced.

The present invention has an aspect to provide a technique for accurately detecting a target molecule.

(1) A method for detecting a target molecule according to a first aspect of the present invention includes the steps of: providing a fluid device having a substrate and a well array disposed on the substrate, supplying a dispersion liquid of a structure including a target molecule into the well array of the fluid device, and introducing the structure into wells of the well array; supplying a sealing solution into the well array, forming a layer of the sealing solution on the dispersion liquid introduced in the wells, and sealing the dispersion liquid in the wells; extracting the target molecule from the structure; and detecting the target molecule.

(2) The step of extracting the target molecule may be performed in the wells.

(3) The step of extracting the target molecule may be performed after the step of sealing the dispersion liquid in the wells.

(4) The step of detecting the target molecule may be performed after the step of extracting the target molecule.

(5) The step of detecting the target molecule may include a signal amplification reaction.

(6) The method may further include a step of detecting the structure.

(7) The step of detecting the target molecule and the step of detecting the structure may be performed at the same time. (8) In the step of detecting the target molecule, two or more types of the target molecule may be detected.

(9) The structure may be at least one of an exosome, cell, bacterium, virus, fungus, and endoplasmic reticulum.

(10) The target molecule may be a nucleic acid or a protein.

(11) In the step of introducing, one or less of the structure may be introduced into each well of the well array.

(12) The step of extracting the target molecule may be performed by using any of physical, chemical, and biological techniques.

(13) The method may further include a step of binding a capture substance to the structure, the capture substance having a specific binding substance to the structure.

(14) The step of introducing the structure may be performed by introducing the capture substance into the wells of the well array.

(15) The specific binding substance may be an antibody.

According to embodiments of the present invention, a technique for accurately detecting a target molecule can be provided.

Embodiments of the present invention have so far been described. However, configurations, combinations of the configurations, and the like of the embodiments are only examples, and additions, omissions, substitutions, or any other changes in configurations may be made without departing from the spirit of the present invention. Further, the present invention should not be limited by these embodiments.

<Industrial Applicability>

According to embodiments of the present invention, it is possible to provide a technique for detecting the target molecule with high accuracy compared with a conventional method in which the target molecules are distributed into the respective wells of a micro array by using a flow path after they are extracted from the structure.

REFERENCE SIGNS LIST

100 . . . fluid device
101 . . . cover member

102 . . . liquid supply port
103 . . . liquid discharge port
104 . . . substrate
105 . . . well
106 . . . flow path
107 . . . reagent solution
108 . . . reagent solution filled in the well
201 . . . sealing liquid
202 . . . micro compartment
301 . . . microdroplets emitting signals 11 . . . target molecule
12 . . . structure
12' . . . structure after extraction
13 . . . specific binding substance
14 . . . capture substance Obviously, numerous modifications and variations of the present invention are possible in light of the above teachings. It is therefore to be understood that within the scope of the appended claims, the invention may be practiced otherwise than as specifically described herein.

What is claimed is:

1. A method for detecting a target molecule, comprising:
providing a fluid device having a flow path and a plurality of wells arrayed in the fluid device and connected to the flow path;
supplying a liquid dispersion of a structural substance having a target molecule into the fluid device such that the structural substance is distributed into the plurality of wells in the fluid device and has the target molecule in or on the structural substance;
supplying a sealing solution into the fluid device such that a layer of the sealing solution is formed in the flow path in the fluid device and individually seals the plurality of wells containing the liquid dispersion;
extracting the target molecule from the structural substance in the plurality of wells sealed by the layer of the sealing solution in the fluid device such that the liquid dispersion in the plurality of wells includes the structural substance and the target molecule extracted from the structural substance; and
detecting the target molecule extracted from the structural substance in the plurality of wells in the fluid device,
wherein the fluid device includes a substrate and a cover member attached to the substrate such that the plurality of wells is formed in the substrate and that, the flow path is formed between the substrate and the cover member, and the supplying of the sealing solution includes forming the layer of the sealing solution between the substrate and the cover member such that the layer of the sealing solution entirely fills the flow path formed between the substrate and the cover member.

2. The method according to claim 1, wherein the extracting of the target molecule includes extracting the target molecule from the structural substance by using an extracting substance for a chemical technique.

3. The method according to claim 1, wherein the extracting of the target molecule includes extracting the target molecule from the structural substance by using an extracting substance for a biological technique.

4. The method according to claim 1, wherein the extracting of the target molecule includes adjusting an extraction condition in the plurality of wells.

5. The method according to claim 1, wherein the detecting of the target molecule includes immunoassay.

6. The method according to claim 1, wherein the detecting of the target molecule includes an ICA reaction.

7. The method according to claim 1, wherein the detecting of the target molecule includes a signal amplification reaction.

8. The method according to claim 1, further comprising: detecting the structural substance.

9. The method according to claim 8, wherein the detecting of the target molecule and the detecting of the structural substance are conducted in a same process.

10. The method according to claim 1, wherein the structural substance includes a second target molecule, and the detecting includes detecting the target molecule and the second target molecule.

11. The method according to claim 1, wherein the structural substance is at least one of an exosome, cell, bacterium, virus, fungus, and endoplasmic reticulum.

12. The method according to claim 1, wherein the target molecule is a nucleic acid or a protein.

13. The method according to claim 1, wherein the introducing introduces at most one structural substance into each well of the well array.

14. The method according to claim 1, wherein the extracting of the target molecule is conducted by at least one of physical, chemical, and biological techniques.

15. The method according to claim 1, further comprising:
bringing the structural substance into contact with a capture substance having a specific binding substance to the structural substance such that the capture: substance binds to the structural substance.

16. The method according to claim 15, wherein the introducing of the structural substance comprises introducing the capture substance into the plurality of wells in the fluid device.

17. The method according to claim 15, wherein the specific binding substance is an antibody.

18. The method according to claim 11, further comprising:
bringing the structural substance into contact with a capture substance having a specific binding substance to the structural substance such that the capture substance binds to the structural substance.

19. The method according to claim 18, wherein the introducing of the structural substance comprises introducing the capture substance into the plurality of wells in the fluid device.

20. The method according to claim 18, wherein the specific binding substance is an antibody.

* * * * *